(12) United States Patent
Giftakis et al.

(10) Patent No.: US 10,369,353 B2
(45) Date of Patent: Aug. 6, 2019

(54) SEIZURE DISORDER EVALUATION BASED ON INTRACRANIAL PRESSURE AND PATIENT MOTION

(75) Inventors: Jonathon E. Giftakis, Maple Grove, MN (US); Nina M. Graves, Minnetonka, MN (US); Jonathan C. Werder, Corcoran, MN (US); Eric J. Panken, Edina, MN (US); Timothy J. Denison, Minneapolis, MN (US); Keith A. Miesel, St. Paul, MN (US); Michele H. Herzog, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 2642 days.

(21) Appl. No.: 12/359,037

(22) Filed: Jan. 23, 2009

(65) Prior Publication Data

US 2010/0121213 A1 May 13, 2010

Related U.S. Application Data

(60) Provisional application No. 61/113,441, filed on Nov. 11, 2008.

(51) Int. Cl.
*A61B 5/03* (2006.01)
*A61N 1/05* (2006.01)
(Continued)

(52) U.S. Cl.
CPC ............ *A61N 1/0534* (2013.01); *A61B 5/031* (2013.01); *A61B 5/4094* (2013.01); *A61N 1/36082* (2013.01)

(58) Field of Classification Search
CPC .............................. A61B 5/031; A61B 5/4094
(Continued)

(56) References Cited

U.S. PATENT DOCUMENTS 4,080,653 A 3/1978 Barnes, Jr. et al.
4,320,766 A 3/1982 Alihanka et al.
(Continued)

FOREIGN PATENT DOCUMENTS

WO WO 97/42990 11/1997
WO WO 2006/119103 A2 11/2006
(Continued)

OTHER PUBLICATIONS

International Search Report and Written Opinion for corresponding PCT Application No. PCT/US2009/051343, dated Nov. 6, 2009 (11 pgs.).
(Continued)

*Primary Examiner* — Devin B Henson
*Assistant Examiner* — H. Q. Nguyen
(74) *Attorney, Agent, or Firm* — Shumaker & Sieffert, P.A.

(57) ABSTRACT

Intracranial pressure of a patient may be monitored in order to evaluate a seizure disorder. In some examples, trends in the intracranial pressure over time may be monitored, e.g., to detect changes to the patient's condition. In addition, in some examples, a seizure metric may be generated for a detected seizure based on sensed intracranial pressures. The seizure metric may indicate, for example, an average, median, or highest relative intracranial pressure value observed during a seizure, a percent change from a baseline value during the seizure, or the time for the intracranial pressure to return to a baseline state after the occurrence of a seizure. In addition to or instead of intracranial pressure, patient motion or posture may be monitored in order to assess the patient's seizure disorder. For example, a seizure type or severity may be determined based on patient motion sensed during a seizure.

50 Claims, 13 Drawing Sheets

(51) Int. Cl.
*A61B 5/00* (2006.01)
*A61N 1/36* (2006.01)
(58) Field of Classification Search
USPC .......................................................... 600/561
See application file for complete search history.

(56) References Cited

U.S. PATENT DOCUMENTS

| | | | |
|---|---|---|---|
| 4,971,061 | A | 11/1990 | Kageyama et al. |
| 5,304,206 | A | 4/1994 | Baker, Jr. et al. |
| 5,349,962 | A | 9/1994 | Lockard et al. |
| 5,978,702 | A | 11/1999 | Ward et al. |
| 5,995,868 | A * | 11/1999 | Dorfmeister et al. ........ 600/544 |
| 6,248,080 | B1 | 6/2001 | Miesel et al. |
| 6,360,122 | B1 | 3/2002 | Fischell et al. |
| 6,361,508 | B1 | 3/2002 | Johnson et al. |
| 6,560,486 | B1 | 5/2003 | Osorio et al. |
| 6,788,975 | B1 | 9/2004 | Whitehurst et al. |
| 7,006,872 | B2 | 2/2006 | Gielen et al. |
| 7,167,751 | B1 | 1/2007 | Whitehurst et al. |
| 2002/0052563 | A1 | 5/2002 | Penn et al. |
| 2002/0169485 | A1 | 11/2002 | Pless et al. |
| 2003/0236474 | A1 | 12/2003 | Singh |
| 2004/0172089 | A1 | 9/2004 | Whitehurst et al. |
| 2005/0015009 | A1* | 1/2005 | Mourad ................. A61B 5/031 600/438 |
| 2005/0203366 | A1 | 9/2005 | Donoghue et al. |
| 2006/0135877 | A1 | 6/2006 | Giftakis et al. |
| 2006/0212093 | A1 | 9/2006 | Pless et al. |
| 2006/0264777 | A1 | 11/2006 | Drew |
| 2007/0249954 | A1 | 10/2007 | Virag et al. |
| 2007/0255118 | A1 | 11/2007 | Miesel et al. |
| 2007/0276439 | A1 | 11/2007 | Miesel et al. |
| 2008/0061961 | A1 | 3/2008 | John |
| 2008/0071324 | A1 | 3/2008 | Miesel et al. |
| 2008/0319281 | A1 | 12/2008 | Aarts |
| 2008/0319335 | A1 | 12/2008 | Greene |
| 2009/0082640 | A1 | 3/2009 | Kovach et al. |
| 2009/0099624 | A1 | 4/2009 | Kokones et al. |
| 2009/0171168 | A1 | 7/2009 | Leyde et al. |
| 2012/0053491 | A1 | 3/2012 | Nathan et al. |

FOREIGN PATENT DOCUMENTS

| | | |
|---|---|---|
| WO | WO 2006/119103 A3 | 11/2006 |
| WO | WO 2007/034476 A2 | 3/2007 |
| WO | WO 2008/085008 A1 | 7/2008 |
| WO | WO 2008/133626 | 11/2008 |

OTHER PUBLICATIONS

XP002550864, Retrieved from the Internet: URL:web.archive.org/web/20071016060909/http://en.wikipedia.org/wiki/Intracranial_pressure, dated Sep. 28, 2007, retrieved on Oct. 16, 2007 (6 pgs.).
Gabor et al., "Intracranial Pressure During Epileptic Seizures," Electroencephalography and clinical Neurophysiology, 57, pp. 497-506 (Jan. 1984).
U.S. Appl. No. 11/799,051, filed Apr. 30, 2007, entitled "Seizure Prediction" by Denison et al.
U.S. Appl. No. 11/401,100, filed Apr. 10, 2006, entitled "Shifting Between Electrode Combinations in Electrical Stimulation Device", by Goetz et al.
U.S. Appl. No. 61/113,441, filed Nov. 11, 2008, entitled "Seizure Disorder Evaluation Based on Intracranial Pressure and Patient Motion", by Giftakis et al.
U.S. Appl. No. 12/359,055, filed Jan. 23, 2009, entitled "Seizure Disorder Evaluation Based on Intracranial Pressure and Patient Motion", by Giftakis et al.
Office Action dated Jun. 20, 2012 for U.S. Appl. No. 12/359,055, (24 pgs.).
Responsive Amendment dated Sep. 20, 2012 for U.S. Appl. No. 12/359,055, (16 pgs.).
Response to Office Action dated Mar. 7, 2013, from U.S. Appl. No. 12/359,055, filed Apr. 26, 2013, 6 pp.
Advisory Action from U.S. Appl. No. 12/359,055, dated Jun. 3, 2013, 3 pp.
Pre-Appeal Brief Request for Review for U.S. Appl. No. 12/359,055, filed Jun. 7, 2013, 5 pp.
Office Action for U.S. Appl. No. 12/359,055, dated Mar. 7, 2013, 29 pp.
Response to Office Action dated Oct. 28, 2013, from U.S. Appl. No. 12/359,055, filed Jan. 27, 2014, 20 pp.
Final Office Action from U.S. Appl. No. 12/359,055, dated May 21, 2014, 31 pp.
Office Action from co-pending U.S. Appl. No. 12/359,055, dated Oct. 28, 2013, 32 pp.
Office Action from U.S. Appl. No. 12/359,055, dated Dec. 18, 2014, 8 pp.
Response to Office Action dated Dec. 18, 2014, from International U.S. Appl. No. 12/359,055, filed Apr. 15, 2015, 7 pp.
Final Office Action from U.S. Appl. No. 12/359,055, dated Aug. 7, 2015, 9 pp.
Amendment in Response to Final Office Action dated May 21, 2014, from U.S. Appl. No. 12/359,055, dated Sep. 23, 2014, 23 pp.
Response to Notice of Non-Compliant Amendment, from U.S. Appl. No. 12/359,055, dated Nov. 11, 2014, 13 pp.
Sen et al., "Stertorous breathing is a reliably identified sign that helps in the differentiation of epileptic from psychogenic non-epileptic convulsions: An audit," Epilepsy Research, Sep. 2007, pp. 62-64.
Berg et al., "Newly Diagnosed Epilepsy in Children: Presentation at Diagnosis," Epilepsia, vol. 40, No. 4, Apr. 1999, pp. 445-452.
Azar, et al., "Postictal breathing pattern distinguishes epileptic from nonepileptic convulsive seizures," Epilepisa vol. 19, No. 1, Jan. 2008, pp. 132-137.
Response to Final Office Action dated Aug. 7, 2015, from U.S. Appl. No. 12/359,055, filed Oct. 7, 2015, 8 pp.
Cuppens et al., "Detection of Nocturnal Epileptic Seizures of Pediatric Patients Using Accelerometers: Preliminary Results," IEEE Benelux EMBS Symposium, Dec. 6-7, 2007, 4 pp.
Tormans et al., "Nocturnal Monitoring of Pediatric Patients with Epilepsy based on Accelerometers," accessed from http://www.mobilab-khk.be/mobilab/Research/BioMed/Projects/epileptic on Mar. 31, 2009, 2 pp.
Reply Brief from U.S. Appl. No. 12/359,055, filed Sep. 7, 2016, 12 pp.
Decision on Appeal from U.S. Appl. No. 12/359,055, dated Jan. 2, 2018, 20 pp.
Response to Office Action dated May 21, 2014, from co-pending U.S. Appl. No. 12/359,055, filed Jul. 16, 2014, 12 pp.
Examiner's Answer from U.S. Appl. No. 12/359,055, dated Jul. 14, 2016, 11 pp.
Tormans et al., "Nocturnal Monitoring of Pediatric Patients with Epilepsy Based on Accelerometers," Nov. 2007, 3 pp.

* cited by examiner

| DETECTED SEIZURE | ICP CATEGORY | % CHANGE FROM BASELINE | HIGHEST ICP | BASELINE RETURN TIME | SEVERITY RATING |
|---|---|---|---|---|---|
| SEIZURE 1 | NORMAL | 10% | 9 mmHg | 2.3 minutes | 1 |
| SEIZURE 2 | ELEVATED | 60% | 16 mmHg | 3.4 minutes | 3 |
| SEIZURE 3 | HIGH | 150% | 25 mmHg | 40 minutes | 4 |
| • | | • | • | • | • |
| • | | • | • | • | • |
| • | | • | • | • | • |
| • | | • | • | • | • |
| SEIZURE N | HIGH | 300% | 40 mmHg | 91 minutes | 5 |

FIG. 10

SEIZURE DISORDER EVALUATION BASED ON INTRACRANIAL PRESSURE AND PATIENT MOTION

This application claims the benefit of U.S. Provisional Application No. 61/113,441 to Giftakis et al., entitled, "SEIZURE DISORDER EVALUATION BASED ON INTRACRANIAL PRESSURE AND PATIENT MOTION" and filed on Nov. 11, 2008. The entire content of U.S. Provisional Application No. 61/113,441 is incorporated herein by reference.

TECHNICAL FIELD

The disclosure relates to patient monitoring, and, more particularly, to collecting information to evaluate a patient condition.

BACKGROUND

Some neurological disorders, such as epilepsy, are characterized by the occurrence of seizures. Seizures may be attributable to abnormal electrical activity of a group of brain cells. A seizure may occur when the electrical activity of certain regions of the brain, or even the entire brain, becomes abnormally synchronized. The onset of a seizure may be debilitating. For example, the onset of a seizure may result in involuntary changes in body movement, body function, sensation, awareness or behavior (e.g., an altered mental state). In some cases, each seizure may cause some damage to the brain, which may result in progressive loss of brain function over time.

Attempts to manage seizures have included the delivery of electrical stimulation to regions of the brain and/or the delivery of drugs either orally or infused directly into regions of the brain. In electrical stimulation systems, a medical lead is implanted within a patient and coupled to an external or implanted electrical stimulator. The target stimulation site within the brain or elsewhere may differ between patients, and may depend upon the type of seizures being treated by the electrical stimulation system. In some therapy systems, electrical stimulation is continuously delivered to the brain. In other systems, the delivery of electrical stimulation is triggered by the detection or prediction of some event, such as the detection of a seizure based on bioelectrical brain signals sensed within the brain.

In automatic drug delivery systems, a catheter is implanted within a patient and coupled to an external or implanted fluid delivery device. The fluid delivery device may deliver a dose of an anti-seizure drug into the blood stream or into a region of the brain of the patient at regular intervals, upon the detection or prediction of some event, such as the detection of a seizure by electroencephalogram (EEG) or electrocorticogram (ECG) sensors implanted within the brain, or at the direction of the patient or clinician.

SUMMARY

In general, the disclosure is directed toward monitoring intracranial pressure (ICP) of a patient in order to evaluate a patient's seizure disorder, which may include, for example, epilepsy. Intracranial pressure may be monitored via subdurally implanted pressure sensors, which may be located on a therapy delivery element (e.g., an implantable medical lead or an implantable catheter) that delivers therapy to a brain of the patient or may be physically separate from a therapy delivery element.

In some examples, the intracranial pressure of the patient over time may be monitored to determine relatively long-term trends in the intracranial pressure, which may indicate changes to the patient's condition. In addition to or instead of monitoring long-term trends in the patient's intracranial pressure, a seizure metric may be generated based on sensed intracranial pressures. For example, for each detected seizure, a seizure metric may indicate at least one of an average intracranial pressure value during the ictal state (e.g., during a seizure event), a highest relative intracranial pressure value during the ictal state, the percent change from the baseline during the ictal state, the time for the intracranial pressure to return to a baseline state after the occurrence of a seizure, a standard deviation of the intracranial pressure during the seizure relative to the baseline value, or a change in the intracranial pressure values over time during the ictal state. The seizure metrics may be used to assess the patient's seizures, and may help distinguish between different types of seizures.

In addition to or instead of intracranial pressure, patient motion or posture may be monitored in order to assess the patient's seizure disorder. For example, a type of seizure or a severity of the seizure may be determined based on a detected activity level of the patient during a seizure. In addition, a sudden change in patient posture during a time that corresponds to a detected seizure may indicate the patient fell during the seizure.

In one aspect, the disclosure is directed to a method comprising delivering therapy to a patient to manage a seizure disorder, sensing intracranial pressure of the patient, determining a trend in the intracranial pressure over time, and generating an intracranial pressure indication if a value of the intracranial pressure is greater than or equal to a threshold value. The intracranial pressure indication may be stored in a memory of a device, and, in some cases, transmitted to a clinician.

In another aspect, the disclosure is directed to a system comprising a pressure sensor that senses intracranial pressure of a patient, a processor that determines a trend in the intracranial pressure over time, and generates an intracranial pressure indication if a value of the intracranial pressure is greater than or equal to a threshold value.

In another aspect, the disclosure is directed to a system comprising means for sensing intracranial pressure of a patient, means for determining a trend in the intracranial pressure over time, and means for generating an intracranial pressure indication if a value of the intracranial pressure is greater than or equal to a threshold value.

In another aspect, the disclosure is directed to a method comprising sensing intracranial pressure of a patient, detecting a seizure of the patient, determining a seizure metric based on the intracranial pressure, and storing the seizure metric in a memory.

In another aspect, the disclosure is directed to a system a pressure sensor that senses intracranial pressure of a patient, a memory, and a processor that detects a seizure of the patient, determines a seizure metric based on the intracranial pressure, and stores the seizure metric in the memory.

In another aspect, the disclosure is directed to a system comprising means for sensing intracranial pressure of a patient, means for detecting a seizure of the patient, means for determining a seizure metric based on the intracranial pressure, and means for storing the seizure metric in a memory.

In another aspect, the disclosure is directed to a method comprising receiving a signal from a motion sensor, wherein the signal is indicative of motion of a patient, detecting a seizure of the patient, after detecting the seizure, determining a seizure metric based on the signal from the motion sensor, and storing the seizure metric in a memory.

In another aspect, the disclosure is directed to a system comprising a memory, a motion sensor that that generates a signal indicative of patient motion or patient posture, and a processor that receives the signal from the motion sensor, detects a seizure of the patient, and, after detecting the seizure, determines a seizure metric based on the signal from the motion sensor and stores the seizure metric in the memory.

In another aspect, the disclosure is directed to a system comprising means for receiving a signal from a motion sensor, wherein the signal is indicative of motion of a patient, means for detecting a seizure of the patient, means for determining a seizure metric based on the signal from the motion sensor after detecting the seizure, and means for storing the seizure metric in a memory In another aspect, the disclosure is directed to a computer-readable medium comprising instructions. The instructions cause a programmable processor to perform any part of the techniques described herein.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 10 is a conceptual illustration of a table that presents a list of example detected seizures and associated intracranial pressure information.

DETAILED DESCRIPTION

Figure 1:
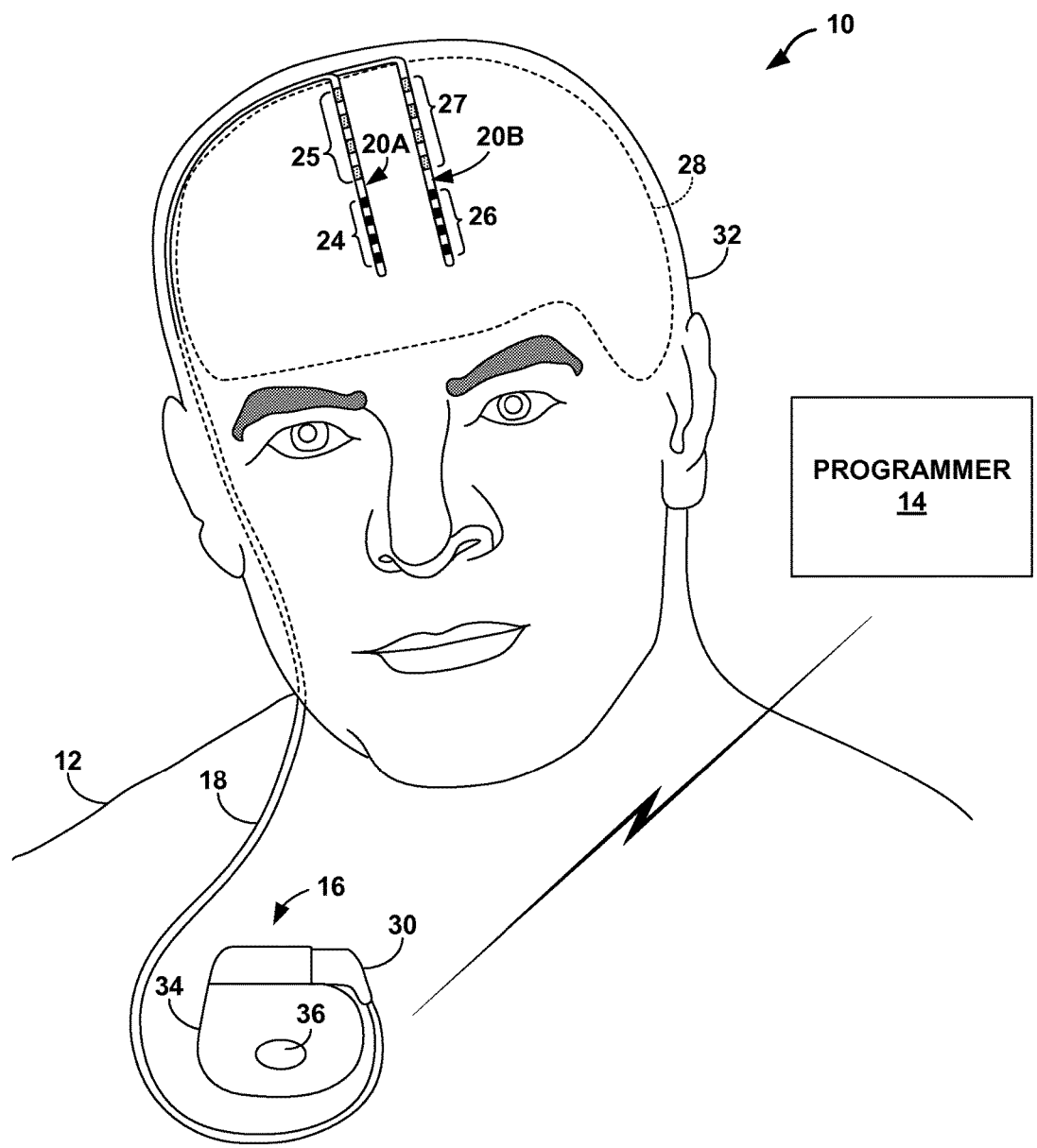
FIG. 1 is a conceptual diagram illustrating an example deep brain stimulation (DBS) system that includes one or more pressure sensors to monitor intracranial pressure of a patient.

FIG. 1 is a conceptual diagram illustrating an example therapy system 10 that delivers therapy to manage a seizure disorder (e.g., epilepsy) of patient 12 that is characterized by the occurrence of seizures. Patient 12 ordinarily will be a human patient. In some cases, however, therapy system 10 may be applied to other mammalian or non-mammalian non-human patients. While seizure disorders are primarily referred to herein, in other examples, therapy system 10 may also provide therapy to manage symptoms of other patient conditions, such as, but not limited to, psychological disorders, movement disorders or other neurogenerative impairment.

Therapy system 10 may be used to manage the seizure disorder of patient 12 by, for example, minimizing the severity of seizures, shortening the duration of seizures, minimizing the frequency of seizures, preventing the onset of seizures, and the like. In addition to delivering therapy to manage a seizure, therapy system 10 monitors one or more physiological parameters of patient 12, including intracranial pressure (ICP), in order to monitor the patient's condition. As described in further detail below, changes to the patient's intracranial pressure or a relatively high intracranial pressure (e.g., a pressure that exceeds a predetermined threshold value) may be a surrogate marker for a change in the condition of the patient's seizure disorder. For example, an intracranial pressure that increases over time may indicate a worsening of the patient's seizure disorder.

In addition, the patient's intracranial pressure during a seizure event may be revealing of the severity of the patient's seizure disorder or at least indicate a change in the patient's seizure disorder. For example, an increase in the number of seizures during which the patient's intracranial pressure values are relatively high may indicate that the type of seizures experienced by patient 12 have changed. A seizure event may include an ictal stage, during which the seizure is actually occurring, and, therefore, the patient's seizure symptoms are present, a pre-ictal stage, which precedes the ictal stage, and the post-ictal stage, which follows the ictal stage. During the ictal and post-ictal stages, manifestations of the seizure may result in changes to the patient's physiological condition. The intracranial pressure of patient 12 may be monitored during the ictal stage, and, in some examples, the pre-ictal and/or post-ictal stages.

Sudden unexpected death in epilepsy (SUDEP) may occur in patients with seizure disorders. SUDEP may also be referred to as sudden unexplained death in epilepsy. Intracranial pressure of patient 12 may be useful for determining whether the status of the patient's seizure disorder has changed, which may indicate whether patient 12 is at risk for SUDEP. In addition, in some cases, a trend in the intracranial pressure of patient 12 over time or the intracranial pressure during the patient's seizures may be useful for detecting when the patient's risk for SUDEP has increased. For example, an increase in the patient's intracranial pressure over time may be indicative of an increased risk of SUDEP. As another example, the occurrence of seizures that are associated with a relatively elevated or high intracranial pressure (e.g., an intracranial pressure that exceeds a threshold value) or an elevated or high intracranial pressure that subsists for a relatively long period of time may be indicative of an increased risk of SUDEP.

An elevated or high intracranial pressure may be determined based on comparison of intracranial pressure to a threshold value, and an elevated or high intracranial pressure that that subsists for a relatively long period may be determined based on a determination of the period of time required for the intracranial pressure to return to a baseline value following a detection of a seizure. The elevated or high intracranial pressure and an elevated or high intracranial pressure that persists for a relatively long period of time may be indicated by seizure metrics that are determined for a detected seizure, as described in further detail below.

While the exact mechanisms by which intracranial pressure may indicate a change in risk of SUDEP for a particular patient 12 are not currently known, monitoring intracranial pressure over time, e.g., during chronic therapy delivery by therapy system 10, may be useful for monitoring the patient's seizure disorder and detecting changes in the patient's physiology (e.g., intracranial pressure) that may be indicative of changes to the patient's risk of SUDEP. Accordingly, therapy system 10, as well as the other therapy systems described herein, includes one or more pressure sensors implanted within cranium 32 of patient 12 to monitor intracranial pressure. In other examples, external pressure sensors may be used alone or in combination with the implanted pressure sensors to monitor intracranial pressure of patient 12.

Although intracranial pressure monitoring is described primarily in combination with therapy systems that deliver therapy to patient to manage a seizure disorder, in other examples, intracranial pressure may be monitored in patients that do not include an implantable or external therapy delivery system that actively delivers therapy to the patient to manage a seizure disorder. For example, a pressure sensor may be implanted in cranium 32 of patient 12 that does not include IMD 16. As an example, a pressure sensor may be implanted as part of a shunt device that helps relieve cerebral spinal fluid from cranium 32 when the intracranial pressure exceeds a threshold value.

Therapy system 10 includes medical device programmer 14, implantable medical device (IMD) 16, lead extension 18, and one or more leads 20A and 20B with respective sets of electrodes 24, 26. Leads 20A, 20B further include respective sets of pressure sensors 25, 27. IMD 16 includes a therapy module that includes a stimulation generator that generates and delivers electrical stimulation therapy to patient 12 via a subset of electrodes 24, 26 of leads 20A and 20B, respectively. In the example shown in FIG. 1, electrodes 24, 26 of leads 20A, 20B are positioned to deliver electrical stimulation to a tissue site within brain 28, such as a deep brain site under the dura mater of brain 28 of patient 12. In some examples, delivery of stimulation to one or more regions of brain 28, such as an anterior nucleus, thalamus or cortex of brain 28, provides an effective treatment to manage a seizure disorder.

In some examples, IMD 16 may also include a sensing module that senses bioelectrical signals within brain 28. The bioelectrical brain signals may reflect changes in electrical current produced by the sum of electrical potential differences across brain tissue. Examples of bioelectrical brain signals include, but are not limited to, an electroencephalogram (EEG) signal, an electrocorticogram (ECOG) signal, a local field potential (LFP) sensed from within one or more regions of a patient's brain and/or action potentials from single cells within the patient's brain.

In some examples, IMD 16 detects the occurrence of a seizure based on the bioelectrical brain signals, which may be used to control therapy delivery to patient 12 in some examples. For example, therapy may be delivered when a bioelectrical brain signal exhibits a certain characteristic, which may be a time domain characteristic (e.g., an amplitude) or a frequency domain characteristic (e.g., an energy level in one or more frequency bands). IMD 16 may use known techniques to correlate a sensed bioelectrical signal with a template in order to detect a seizure, or detect a seizure based on the frequency domain characteristics of a sensed bioelectrical brain signal. An example of a seizure predicting technique is discussed in commonly-assigned U.S. Pat. No. 7,006,872 to Gielen et al., which is entitled, "CLOSED LOOP NEUROMODULATION FOR SUPPRESSION OF EPILEPTIC ACTIVITY" and issued on Feb. 28, 2006. U.S. Pat. No. 7,006,872 to Gielen et al. is incorporated herein by reference in its entirety. U.S. Pat. No. 7,006,872 to Gielen et al. describes a technique for predicting a likelihood of an occurrence of a seizure based on whether a sensed EEG starts to show synchrony as opposed to the normal stochastic features.

Another example of a technique for detecting a seizure is described in commonly-assigned U.S. patent application Ser. No. 11/799,051 to Denison et al., which is entitled, "SEIZURE PREDICTION" and was filed on Apr. 30, 2007. U.S. patent application Ser. No. 11/799,051 to Denison et al. is incorporated herein by reference in its entirety. In an example technique described in U.S. patent application Ser. No. 11/799,051 to Denison et al., a likelihood of an onset of a seizure is determined based on an impedance of one or more regions of the brain of a patient. In some examples described in U.S. patent application Ser. No. 11/799,051 to Denison et al., a relationship between the measured impedance of the brain and an absolute threshold impedance value is used to predict a seizure. In other examples described in U.S. patent application Ser. No. 11/799,051 to Denison et al., a measured impedance signal is analyzed for slope, amplitude, temporal correlation or frequency correlation with a template signal, or combinations thereof in order to determine whether a seizure is likely to occur. In some examples, IMD 16 may include an impedance sensing module to sense impedance of brain tissue.

IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic housing 34 to substantially enclose components, such as a processor, therapy module, and memory.

Implanted lead extension 18 is coupled to IMD 16 via connector 30. In the example of FIG. 1, lead extension 18 traverses from the implant site of IMD 16 and along the neck of patient 12 to cranium 32 of patient 12 to access brain 28. Lead extension 18 is electrically and mechanically connected to leads 20A, 20B (collectively "leads 20"). In the example shown in FIG. 1, leads 20 are implanted within the right and left hemispheres, respectively, of patient 12 in order to deliver electrical stimulation to one or more regions of brain 28, which may be selected based on the patient condition or disorder controlled by therapy system 10. Other implant sites for leads 20 and IMD 16 are contemplated. For example, IMD 16 may be implanted on or within cranium 32 or leads 20 may be implanted within the same hemisphere or IMD 16 may be coupled to a single lead. Although leads 20 are shown in FIG. 1 as being coupled to a common lead extension 18, in other examples, leads 20 may be coupled to IMD 16 via separate lead extensions or directly connected to connector 30. In addition, in some examples, therapy system 10 may include more than two leads or one lead.

Leads 20 may be positioned to deliver electrical stimulation to one or more target tissue sites within brain 28 to manage patient symptoms associated with a seizure disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under the dura mater of brain 28 via a burr hole in cranium 32 of patient 12, and electrically coupled to IMD 16 via one or more leads 20.

In the example shown in FIG. 1, electrodes 24, 26 of leads 20 are shown as ring electrodes. Ring electrodes may be useful in DBS applications because they are relatively simple to program and are capable of delivering an electrical field to any tissue adjacent to electrodes 24, 26. In other examples, electrodes 24, 26 may have different configurations. For examples, in some examples, at least some of the electrodes 24, 26 of leads 20 have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed to a specific direction from leads 20 to enhance therapy efficacy and reduce possible adverse side effects from stimulating a large volume of tissue. In some examples, housing 34 of IMD 16 includes one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 12.

Leads 20 may also be placed within brain 28 to position pressure sensors 25, 27 such that pressure sensors 25, 27 are capable of sensing pressure changes within cranium 32. For example, just as with electrodes 24, 26, pressure sensors 25, 27 may be surgically implanted under the dura mater of brain 28 via a burr hole in cranium 32 of patient 12, and electrically coupled to IMD 16 via one or more leads 20. Pressure sensors 25, 27 each comprise any suitable sensor that generates an electrical signal indicative of pressure at the site in which the pressure sensor is located. Thus, when implanted in cranium 32, as shown in FIG. 1, pressure sensors 25, 27 may each generate an electrical signal that changes as a function of intracranial pressure of patient 12. Intracranial pressure may refer to pressure exerted by cranium 32 on brain tissue, cerebrospinal fluid (CSF), and the blood that may be circulating within brain 28. For example, increased CSF or blood volume may cause increase intracranial pressure. Examples of suitable pressure sensors that may be carried by leads 20 may include, but are not limited to, capacitive or piezoelectric absolute pressure sensors, piezoresistive pressure transducers, or optical pressure sensors that include a pressure-sensitive diaphragm that changes diffraction grating based on pressure exerted on the diaphragm.

An example of a pressure sensor that may be used to monitor intracranial pressure in accordance with the techniques of the disclosure are described in U.S. Pat. No. 6,248,080 to Miesel et al., which is entitled, "INTRACRANIAL MONITORING AND THERAPY DELIVERY CONTROL DEVICE, SYSTEM AND METHOD" and issued on Jun. 19, 2001. U.S. Pat. No. 6,248,080 to Miesel et al. is incorporated herein by reference in its entirety.

Although leads 20 include a plurality of pressure sensors 25, 27, IMD 16 may selectively sense intracranial pressure with one or more of the pressure sensors 25, 27. For example, IMD 16 may select one of the sensors 25, 27 with which to sense intracranial pressure based on the specific location of the sensor 25, 27 within brain 28. In some examples, it is desirable to sense intracranial pressure within a ventricle of brain 28. Thus, by implanting a plurality of pressure sensors 25, 27 that are spaced from each other within patient 12, IMD 16 increases a possibility that one of the sensors 25, 27 are located within a ventricle after leads 20 are implanted within patient 12. In other examples, pressure sensors 25, 27 are implanted at any suitable location within brain 28.

In some cases, the primary objective of a clinician when implanting leads 20 is to position electrodes 24, 26 within target structures (e.g., a thalamus) of brain 28. Accordingly, the placement of sensors 25, 27 within brain 28 may be inadvertent and not specifically selected to monitor intracranial pressure within brain 28. By including a plurality of pressure sensors 25, 27 on leads 20, the possibility that one of the pressure sensors 25, 27 is positioned to generate a electrical signal indicative of intracranial pressure in a desirable location within brain 28 is increased. In some examples, pressure sensors 25, 27 are arranged on leads 20 such that when at least some of electrodes 24, 26 are implanted proximate the anterior nucleus or thalamus of brain 28, at least one of the pressure sensors 25, 27 is located within a ventricle of brain 28.

IMD 16 may include a processor that receives the signals from pressure sensors 25, 27 in order to monitor intracranial pressure of patient 12. In the example shown in FIG. 1, the signals generated by pressure sensors 25, 27 are conducted to the processor within IMD 16 via conductors within the respective lead 20A, 20B. As described in further detail below, the processor of IMD 16 or another device (e.g., programmer 14) monitors the change in the patient's intracranial pressure over time based on the sensed intracranial pressures. The change in the patient's intracranial pressure over time may be indicative of a change in the patient's seizure disorder condition.

In the example shown in FIG. 1, pressure sensor 36 is located on housing 34 of IMD 16 and may be used correct for changes to intracranial pressure sensed by sensors 25, 27 that may be attributable to changes in atmospheric pressure. In some examples, housing 34 may be implanted within subcutaneous tissue of patient 12, and, therefore, may be useful for monitoring atmospheric pressure.

In some examples, the processor of IMD 16 or another device (e.g., programmer 14) determines a seizure metric based on the sensed intracranial pressure. The seizure metric may be determined for each detected seizure. The seizure metric may be used to assess the severity of a seizure or at least distinguish between different types of seizures. In some examples, the seizure metric includes, for each detected seizure, at least one of an average intracranial pressure value during an ictal state (e.g., during a seizure event), a highest intracranial pressure value during the ictal state, the percent change from the baseline during the ictal state, the time for the intracranial pressure to return to a baseline state after the ictal state, the variation (e.g., standard deviation) from a predetermined intracranial pressure value or a mean or median intracranial pressure value, and a slope (a change over time) of the intracranial pressure values during an ictal state.

Although FIG. 1 illustrates pressure sensors 25, 27 located proximal to electrodes 24, 26 on leads 20, in other examples, electrodes 24, 26 and pressure sensors 25, 27 may have any suitable arrangement. For example, one or more pressure sensors 25, 27 may be located between one or more electrodes 24, 26, respectively. As another example, one or more pressure sensors 25, 27 may be located distal to one or more electrodes 24, 26. In addition, as described with respect to FIG. 2, a therapy system may include a pressure sensor that is physically separate from leads that deliver therapy to patient 12, and communicates with IMD 16 via wireless communication techniques or a wired connection. Moreover, in some examples, one or more pressure sensors may be carried by a therapy delivery element other than a lead, such as a catheter that delivers a therapeutic agent to patient 12, as described with respect to FIG. 3.

Various physiological parameters of patient 12 may be extracted from intracranial pressure sensed by pressure sensors 25, 27. For example, intracranial pressure may pulsate as a heart of patient 12 contracts. Thus, in some examples, IMD 16 or programmer 14 may determine heart rate or respiration rate based on the electrical signal indicative of intracranial pressure. In some examples, heart rate and respiration rate are also useful for determining whether the patient's risk of SUDEP has increased or whether the patient's condition has changed.

In some examples, therapy system 10 also includes an implantable or external motion sensor that generates an electrical signal indicative of patient activity level or patient motion. Examples of motion sensors include, but are not limited to, 2-axis or 3-axis accelerometers or piezoelectric crystals. In the example shown in FIG. 1, the motion sensor is located within outer housing 34 of IMD 16. In other examples, a motion sensor may be located on one of the leads 20, on a separate lead electrically connected to IMD 16 or may be physically separate from leads 20 and IMD 16, such as enclosed in a separate outer housing that is implanted within patient 12 or external to patient 12. In examples in which the motion sensor is not implanted within patient 12, the motion sensor may be coupled to patient 12 at any suitable location and via any suitable technique. For example, an accelerometer may be coupled to a leg, torso, wrist, or head of patient 12.

The processor of IMD 16 may analyze the output from the motion sensor to determine a current patient activity level or patient posture, which may be used to evaluate detected seizures. For example, as described in further detail below with reference to FIGS. 12 and 13, the processor of IMD 16 (or a processor of another device, such as programmer 14) may determine whether patient 12 was convulsing during a detected seizure, whether patient 12 fell during a detected seizure, whether an electrographic seizure (as indicated by an EEG or an ECG signal) is associated with motor components (e.g., movement of patient 12 characteristic of a seizure) or the general patient activity level during a seizure. In addition, in some examples, the processor of IMD 16 generates a patient notification if an increase in intracranial pressure (e.g., at or above a threshold value) is detected while patient 12 is in a particular patient posture, such as a prone position. The patient posture may be, for example, a posture associated with a higher incidence of SUDEP.

Electrical stimulation generated by IMD 16 may be configured to manage a variety of disorders and conditions. In some examples, the stimulation generator of IMD 16 is configured to generate and deliver electrical pulses to patient 12 via electrodes of a selected combination of electrodes 24, 26 (referred to as an "electrode combination"). However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may define values for a set of therapy parameters, such as a stimulation electrode combination for delivering stimulation to patient 12, pulse frequency, pulse width, and a current or voltage amplitude of the pulses. A stimulation electrode combination may indicate the specific electrodes 24, 26 that are selected to deliver stimulation signals to tissue of patient 12 and the respective polarities of the selected electrodes.

In the example shown in FIG. 1, IMD 16 includes a memory to store a plurality of therapy programs that each defines a set of therapy parameter values. In some examples, IMD 16 may select a therapy program from the memory based on various parameters, such as based on one or more characteristics of a bioelectrical brain signal, based on the time of day, and the like. IMD 16 may generate electrical stimulation according to the therapy parameter values defined by the selected therapy program to manage the patient symptoms associated with a seizure disorder.

During a trial stage in which IMD 16 is evaluated to determine whether IMD 16 provides efficacious therapy to patient 12, a plurality of therapy programs may be tested and evaluated for efficacy. Therapy programs may be selected for storage within IMD 16 based on the results of the trial stage. During chronic therapy in which IMD 16 is implanted within patient 12 for delivery of therapy on a non-temporary basis, IMD 16 may generate and deliver stimulation signals to patient 12 according to different therapy programs. In addition, in some examples, patient 12 may modify the value of one or more therapy parameter values within a single given program or switch between programs in order to alter the efficacy of the therapy as perceived by patient 12 with the aid of programmer 14. IMD 16 may store instructions defining the extent to which patient 12 may adjust therapy parameters, switch between programs, or undertake other therapy adjustments. Patient 12 may generate additional programs for use by IMD 16 via external programmer 14 at any time during therapy or as designated by the clinician.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multifunction device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the arrangement of pressure sensors 25, 27 on leads 20, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that may provide efficacious therapy to patient 12 to address symptoms associated with the seizure disorder. For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient (e.g., heart rate, respiratory rate or muscle activity). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

Although FIG. 1 illustrates leads 20 that each include four pressure sensors 25, 27, in other examples, therapy delivery elements may include any suitable number of pressure sensors, such as one, two, three or greater than four sensors. In some examples, in addition to or instead of pressure sensors 25, 27 on leads 20, a therapy system includes one or more pressure sensors that are physically separate from a therapy delivery element. Examples of therapy delivery elements include, for example, an implantable medical lead that includes electrodes for delivering stimulation to a tissue site within patient 12 or an implantable catheter that delivers a therapeutic agent (e.g., a drug) to a tissue site within patient 12.

Figure 2:
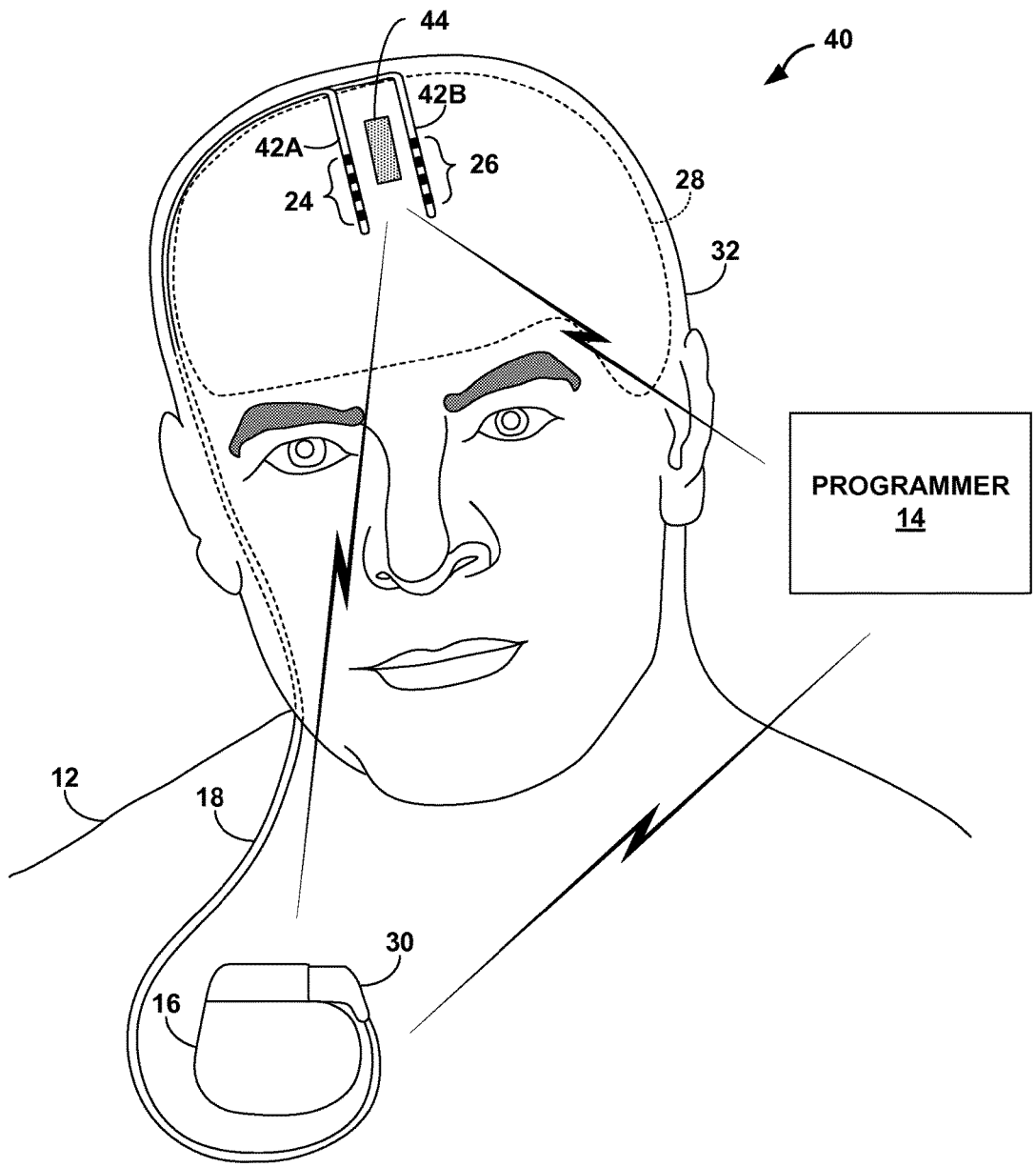
FIG. 2 is a conceptual diagram illustrating another example DBS system that includes one or more pressure sensors to monitor intracranial pressure of a patient.

FIG. 2 is a conceptual illustration of therapy system 40, which includes programmer 14, IMD 16, and lead extension 18 that electrically connects leads 42A, 42B to IMD 16. Leads 42A, 42B (collectively "leads 42") may be similar to leads 20 of FIG. 1, but do not include pressure sensors 25, 27. Instead, therapy system 40 includes pressure sensor 44 implanted within cranium 32 of patient 12 to sense intracranial pressure. In some examples, pressure sensor 44 is located subdurally and within a ventricle of brain 28.

Pressure sensor 44 may comprise any suitable pressure sensor, such as a capacitive or piezoelectric absolute pressure sensor. In the example shown in FIG. 2, pressure sensor 44 is mechanically decoupled from leads 42 and substantially self-contained. This enables a clinician to implant pressure sensor 44 independently of leads 42. In addition, pressure sensor 44 that is mechanically separate from leads 42 and substantially self-contained may be useful for retro-fitting existing therapy systems to include a sensor that generates a signal indicative of intracranial pressure.

Pressure sensor 44 transmits an electrical signal indicative of intracranial pressure to IMD 16 via wireless communication techniques, such as RF communication techniques, as shown in FIG. 2, or via a wired communication technique. For example, a lead other than leads 42 carrying stimulation electrodes 24, 26 may be used to electrically connect pressure sensor 44 to IMD 16. Pressure sensor 44 and IMD 16 may communicate directly or via another device, such as programmer 14, which may function as a telemetry link for IMD 16 and pressure sensor 44.

Although FIG. 2 illustrates therapy system 40 including a single pressure sensor 44, in other examples, therapy system 40 may include any suitable number of pressure sensors, which may or may not be physically separate from leads 42. For example, therapy system 40 may include two, three, four or more physically separate and self-contained pressure sensors 44. As another example, leads 42 may carry one or more pressure sensors in addition to pressure sensor 44. In addition, in some examples, pressure sensor 44 that is physically separate from IMD 16 and leads 42 includes a motion sensor (e.g., a 2-axis or 3-axis accelerometer). However, other components of therapy system 40 may also include a motion sensor and/or a motion sensor may be physically separate from leads 42, pressure sensor 44, IMD 16 and separately implanted within patient 12 or carried externally to patient 12.

Figure 3:
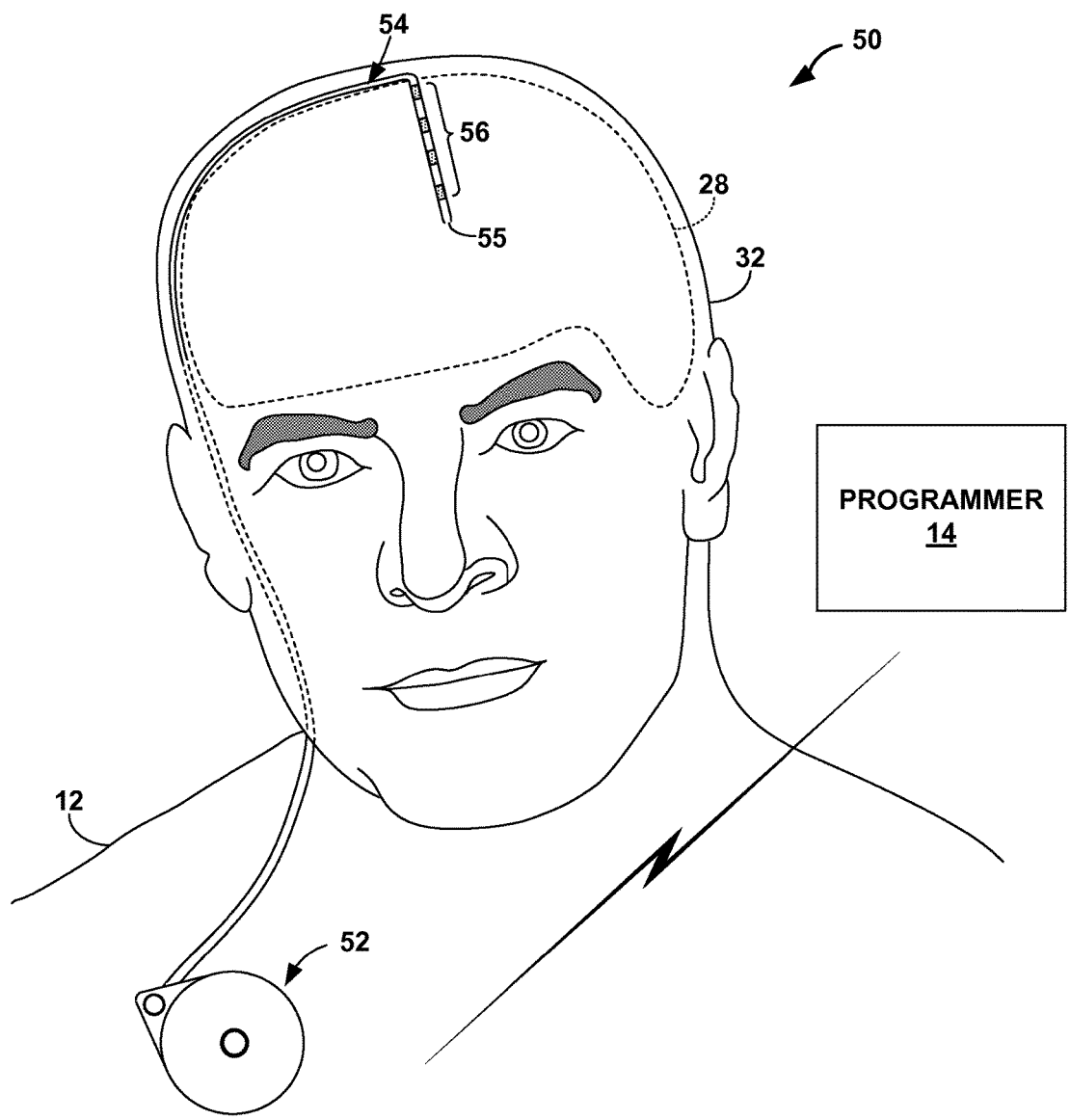
FIG. 3 is a conceptual diagram illustrating an example therapy system in which a therapeutic agent is delivered to a tissue site within a brain of a patient, where the therapy system includes one or more pressure sensors to monitor intracranial pressure of a patient.

FIG. 3 is a conceptual diagram of therapy system 50, which includes IMD 52 and catheter 54, which includes a plurality of pressure sensors 56. IMD 52 is configured to deliver at least one therapeutic agent, such as a pharmaceutical agent (e.g., anti-seizure medication), anti-inflammatory agent, gene therapy agent, or the like, to a target tissue site within brain 28 of patient 11 via catheter 54, which is in fluid communication with IMD 52. Catheter 54 may be coupled to IMD 52 either directly or with the aid of an extension (not shown in FIG. 1).

In some examples, IMD 52 includes a fluid pump or another device that delivers a therapeutic agent in some metered or other desired flow dosage to the therapy site within patient 12 from a reservoir within IMD 52 via catheter 54. Examples of pharmaceutical agents that IMD 52 may deliver to patient 12 to manage a seizure disorder include, but are not limited to, lorazepam, carbamazepine, oxcarbazepine, valproate, divalproex sodium, acetazolamide, diazepam, phenytoin, phenytoin sodium, felbamate, tiagabine, levetiracetam, clonazepam, lamotrigine, primidone, gabapentin, phenobarbital, topiramate, clorazepate, ethosuximide, and zonisamide. Other therapeutic agents may also provide effective therapy to manage the patient's seizure disorder, e.g., by minimizing the severity, duration, and/or frequency of the patient's seizures. In other examples, IMD 52 delivers a therapeutic agent to tissue sites within patient 12 other than brain 28.

Pressure sensors 56 may be similar to pressure sensors 25, 27 (FIG. 1), and are configured to generate an electrical signal indicative of intracranial pressure of patient 12. Although FIG. 3 illustrates catheter 54 including four pressure sensors 56, in other examples, a catheter may include any suitable number of pressure sensors, such as one, two, three or greater than four. In addition, although pressure sensors 56 are located proximal to the fluid delivery port 55 of catheter 54 in the example shown in FIG. 3, in other examples, one or more of pressure sensors 56 may be distal to fluid delivery port 55 of catheter 54. Catheter 54 may include more than one fluid delivery port. Thus, in some examples, one or more pressure sensors 55 may be located between fluid delivery ports of catheter 54.

Although not shown in FIG. 3, in some examples, catheter 54 includes one or more electrodes for sensing bioelectrical brain signals of patient 12. The bioelectrical brain signals may be useful for detecting a seizure and monitoring the patient's brain activity to manage the seizure disorder of patient 12.

While the remainder of the disclosure describes various systems, devices, and techniques for monitoring intracranial pressure of patient 12 and generating seizure metrics based on sensed intracranial pressure of patient 12 with respect to therapy system 10 of FIG. 1, the systems, devices, and techniques described herein are also applicable to therapy systems 40 (FIG. 2) and 50 (FIG. 3), as well as any other therapy system that may include a pressure sensor configured to sense intracranial pressure of patient 12. In some cases, the therapy system may be used for monitoring intracranial pressure of patient 12 and may not include therapy delivery (e.g., stimulation delivery or therapeutic agent delivery) capabilities.

Figure 4:
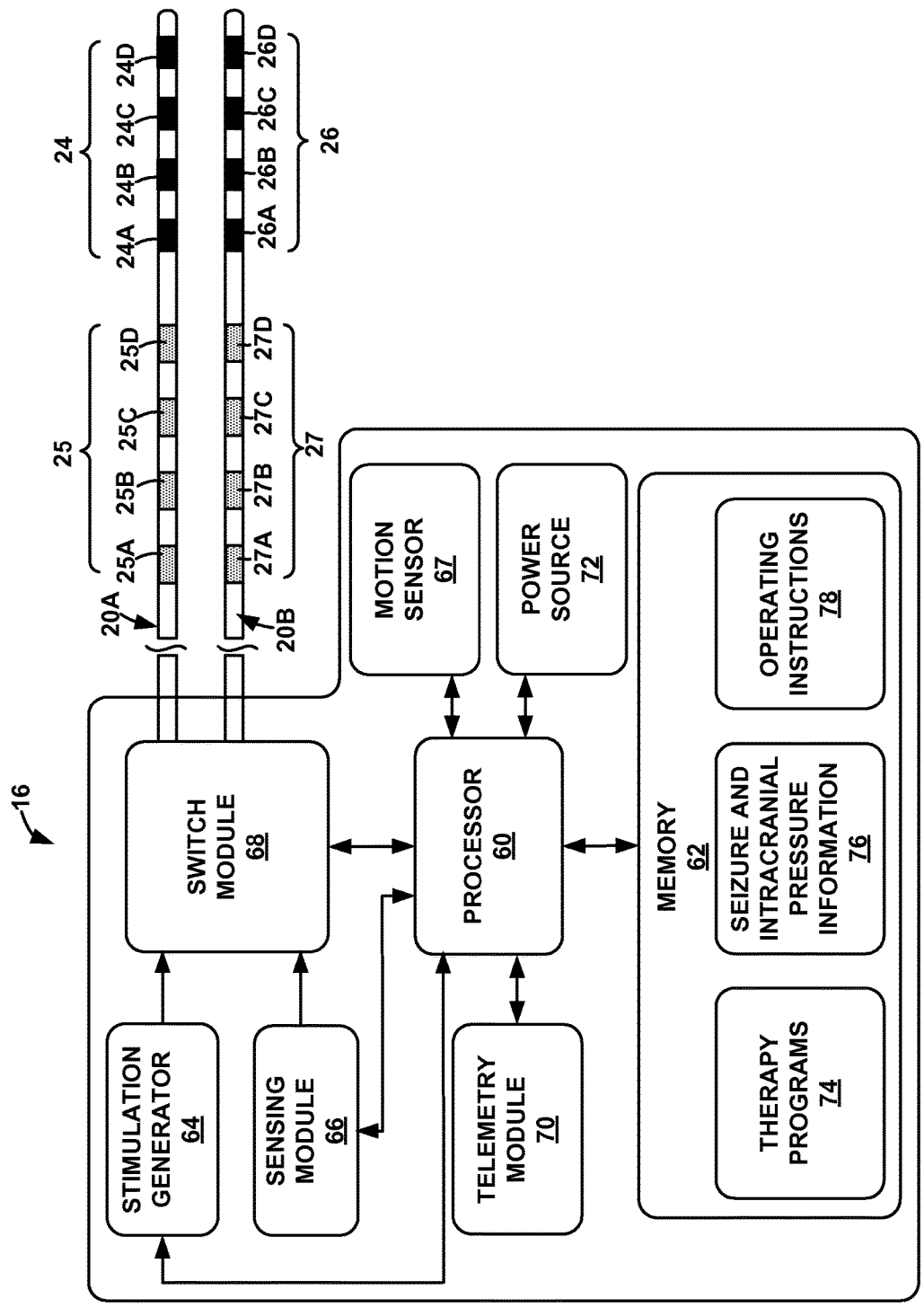
FIG. 4 is functional block diagram illustrating components of an example medical device.

FIG. 4 is a functional block diagram illustrating components of an example IMD 16. In the example shown in FIG. 4, IMD 16 includes processor 60, memory 62, stimulation generator 64, sensing module 66, motion sensor 67, switch module 68, telemetry module 70, and power source 72. Memory 62 may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 4, memory 62 stores therapy programs 74, seizure and intracranial pressure information 76, and operating instructions 78 in separate memories within memory 62 or separate areas within memory 62. Each stored therapy program 74 defines a particular program of therapy in terms of respective values for electrical stimulation parameters, such as a stimulation electrode combination, electrode polarity, current or voltage amplitude, and, in if stimulation generator 64 generates and delivers stimulation pulses, the therapy programs may define values for a pulse width, pulse rate, and duty cycle of a stimulation signal. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Seizure and intracranial pressure information 76 stored by memory 62 includes intracranial pressure data generated by sensing module 66 via at least one of pressure sensors 25, 27. For example, the electrical signals generated by one or more of the pressure sensors 25, 27 that indicate intracranial pressure may be stored by memory 62 as seizure and intracranial pressure information 76. In addition, information relating to the actual occurrence of seizures, such as a seizure indication generated when processor 60 detects a seizure (e.g., based on bioelectrical brain signals or patient input), may be stored by memory 62 as seizure and intracranial pressure information 76. In some examples, processor 60 may detect a seizure based on bioelectrical brain signals sensed by sensing module 66 via a subset of electrodes 24, 26. Thus, in some examples, processor 60 stores the bioelectrical brain signals as seizure and intracranial pressure information 76. Operating instructions 78 guide general operation of IMD 16 under control of processor 60, and may include instructions for measuring the impedance of electrodes 24, 26 and/or determining the distance between electrodes 24, 26.

Stimulation generator 64, under the control of processor 60, generates stimulation signals for delivery to patient 12 via selected combinations of electrodes 24, 26. In some examples, stimulation generator 64 generates and delivers stimulation signals to anterior nucleus of the thalamus of brain 28 (FIG. 1) of patient 12 via a select combination of electrodes 24, 26, where the stimulation signals have a frequency in a range of about 3 Hertz (Hz) to about 250 Hz, a voltage of about 0.1 volts to about 10.5 volts, and a pulse width of about 60 microseconds to about 450 microseconds. In some examples, the stimulation signals have a frequency of 120 Hz, a voltage of about 4 volts, and a pulse width of about 100 microseconds. In addition, in some examples, the stimulation signals have a frequency of 145 Hz, a voltage of about 5 volts, and a pulse width of about 145 microseconds. In addition, the stimulation signals may have any suitable therapy cycle, which includes an on-cycle during which therapy is delivered to patient 12 and an off-cycle during which therapy is not delivered to patient 12. For example, a therapy cycle may have an on-cycle of about thirty seconds to about five minutes (e.g., about one minute) and an off-cycle of about thirty seconds to about five minutes (e.g., about five minutes).

Other stimulation targets within brain 28, other stimulation parameter values, and other therapy cycles are contemplated. Other ranges of therapy parameter values may also be useful, and may depend on the target stimulation site within patient 12, which may or may not be within brain 28. While stimulation pulses are described, stimulation signals may be of any form, such as continuous-time signals (e.g., sine waves) or the like.

In each of the examples described herein, if stimulation generator 64 shifts the delivery of stimulation energy between two therapy programs and/or two different electrode combinations, processor 60 of IMD 16 may provide instructions that cause stimulation generator 64 to time-interleave stimulation energy between the electrode combinations of the two therapy programs, as described in commonly-assigned U.S. patent application Ser. No. 11/401,100 by Steven Goetz et al., entitled, "SHIFTING BETWEEN ELECTRODE COMBINATIONS IN ELECTRICAL STIMULATION DEVICE," and filed on Apr. 10, 2006, the entire content of which is incorporated herein by reference. In the time-interleaved shifting example, the amplitudes of the stimulation signals delivered via the electrode combinations of the first and second therapy program are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off. Other techniques for shifting the delivery of stimulation signals between two therapy programs and/or electrode combinations may be used in other examples.

Processor 60 may include any one or more of a microprocessor, a controller, a digital signal processor (DSP), an application specific integrated circuit (ASIC), a field-programmable gate array (FPGA), discrete logic circuitry, and the functions attributed to processor 60 herein may be embodied as firmware, hardware, software or any combination thereof. Processor 60 controls stimulation generator 64 according to therapy programs 74 stored in memory 62 to apply particular stimulation parameter values specified by one or more programs, such as amplitude, pulse width, and pulse rate.

In the example shown in FIG. 4, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Stimulation generator 64 may be a single channel or multi-channel stimulation generator. In particular, stimulation generator 64 may be capable of delivering, a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66 is configured to sense bioelectrical brain signals of patient 12 via a selected subset of electrodes 24, 26. Processor 60 may control switch module 68 to electrically connect sensing module 66 to selected combinations of electrodes 24, 26. In this way, sensing module 66 may selectively sense bioelectrical brain signals with different combinations of electrodes 24, 26. As previously described, in some examples, processor 60 may detect a seizure of patient 12 via the sensed bioelectrical brain signal.

A seizure detected by detecting certain characteristics of sensed bioelectrical brain signal may be referred to as an electrographic seizure. In some cases, an electrographic seizure is associated with motor component. During an electrographic seizure that is associated with a motor component, patient 12 may undergo motions, e.g., a repetitive motion, that are characteristic of a seizure rather than other patient motions (e.g., day-to-day activities such as walking, running, riding in a car, and the like). An electrographic seizure that is associated with a motor component is also referred to as a motor seizure. In contrast, an electrographic seizure that is not associated with a motor component may be referred to as a sensory seizure.

In other examples, processor 60 may detect a seizure of patient 12 based on impedance of tissue within brain 28, which may be sensed via any suitable combination of electrodes 24, 26. For example, as described in U.S. patent application Ser. No. 11/799,051 to Denison et al., an impedance of brain 28 (FIG. 1) of patient 12 is measured by delivering a stimulation current to brain 28 via implanted electrodes. The stimulation current may be relatively low to prevent inadvertent stimulation of tissue and to prevent patient 12 from feeling the stimulation current. For example, the stimulation current may be in a range of about 500 nanoamps (nA) to about 10 microamps (μA), although other stimulation currents may be used. The stimulation current that is delivered to measure impedance may differ from that used to deliver stimulation therapy to the patient to prevent a seizure from occurring or to mitigate the effects of a seizure. As described in U.S. patent application Ser. No. 11/799,051 to Denison et al., examples of frequencies that may be used for the input stimulation current to measure impedance of the brain include, but are not limited to range of about 1 kilohertz (kHz) to about 100 kHz, such as a range of about 4 kHz to about 16 kHz.

In addition to sensing bioelectrical brain signals, sensing module 66 is configured to sense intracranial pressure of patient 12 via a selected one or more pressure sensors 25, 27. In the example shown in FIG. 4, the set of pressure sensors 25 of lead 20A includes electrodes 25A, 25B, 25C, and 25D, and the set of pressure sensors 27 of lead 20B includes electrodes 27A, 27B, 27C, and 27D. Processor 60 may control switch module 68 to electrically connect sensing module 66 to one or more selected pressure sensors 25, 27. The one or more pressure sensors 25, 27 that are used to sense intracranial pressure of patient 12 may be selected based on the location of the respective pressure sensors 25, 27 within brain 28.

Although sensing module 66 is incorporated into a common housing 34 with stimulation generator 64 and processor 60 in FIG. 4, in other examples, sensing module 66 is in a separate outer housing from outer housing 34 of IMD 16 and communicates with processor 60 via wired or wireless communication techniques.

In the example shown in FIG. 4, IMD 16 includes motion sensor 67, which is enclosed with a common housing with processor 60, stimulation generator 64, and sensing module 66. As previously described, in other examples, motion sensor 67 is connected to a lead and/or implanted separately from IMD 16 within patient 12, or may be external to patient 12. Motion sensor 67 may comprise any suitable device that generates an electrical signal that is indicative of patient activity level or patient posture. For example, motion sensor 67 may comprise a single axis, 2-axis or 3-axis accelerometer or a piezoelectric crystal. Signals from motion sensor 67 are provided to processor 60, which may determine a patient activity level or patient posture using any suitable technique, such as template matching or comparison to a motion sensor output stored in memory 62.

As described in further detail below with reference to FIGS. 12 and 13, processor 60 may associate signals from motion sensor 67 with detected seizures. The motion sensor signals may be stored as seizure information 76 in memory 62 of IMD 16. Processor 60 may determine various seizure metrics based on the output from motion sensor 67 that is associated with a seizure. For example, processor 60 may determine a seizure metric that indicates whether a detected seizure was convulsive or nonconvulsive, or a sensory seizure or a motor seizure. As another example, based on the output from motions sensor 67, processor 60 may determine a seizure metric that indicates whether patient 12 underwent a sudden change in posture after the detection of a seizure.

In some examples, intracranial pressure information from sensing module 66 may also be used to determine patient posture. For example, a particular intracranial pressure value may be associated with a particular patient posture in memory 62 of IMD 16. Thus, processor 60 may detect a particular intracranial pressure value after detecting a seizure, and determine a patient posture based on the intracranial pressure value. A change in patient posture from a pre-ictal stage to an ictal stage may indicate that patient 12 fell during the seizure, which may indicate that the seizure was relatively severe. In this way, intracranial pressure (as well as motion sensor 67) may be useful for distinguishing between severe seizures and relatively minor seizures. A relatively severe seizure, e.g., a tonic-clonic seizure, may be characterized by changes in muscle tone and involuntary movements.

Telemetry module 70 supports wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by radiofrequency (RF) communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit seizure and intracranial pressure information 76 to programmer 14 via telemetry module 70.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 5:
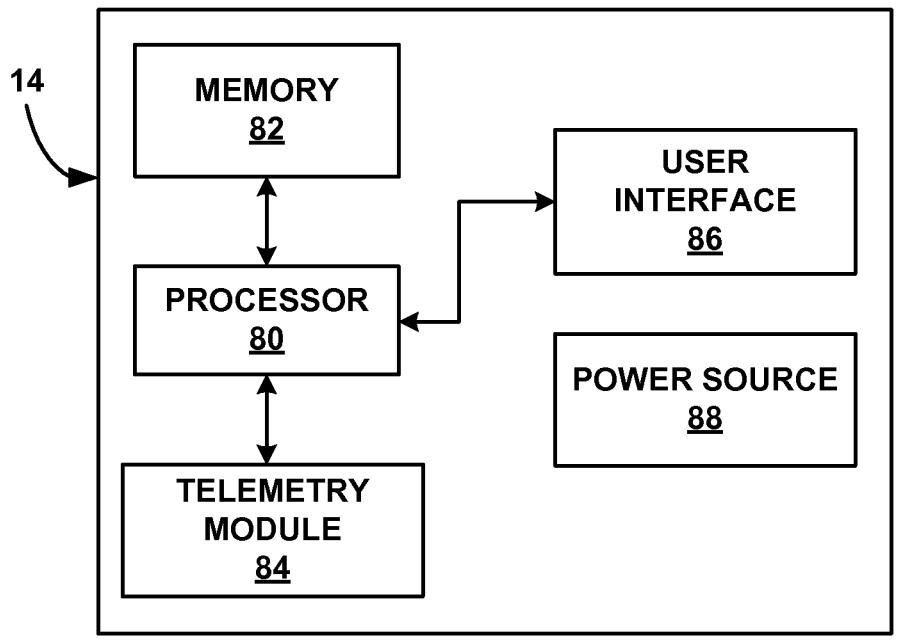
FIG. 5 is a functional block diagram illustrating components of an example medical device programmer.

FIG. 5 is a conceptual block diagram of an example external medical device programmer 14, which includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, to present information related to the therapy, such as information related to bioelectrical signals sensed via a plurality of sense electrode combinations. In addition, user interface 86 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 80 of programmer 14 and provide input.

If programmer 14 includes buttons and a keypad, the buttons may be dedicated to performing a certain function, i.e., a power button, or the buttons and the keypad may be soft keys that change function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display. In other examples, user interface 86 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 80 of programmer 14. For example, in some examples, processor 80 may receive intracranial pressure information from IMD 16 or from a sensing module that is separate from IMD 16. The separate sensing module may, but need not be, implanted within patient 12. In some examples, processor 80 may evaluate the seizure disorder of patient 12, e.g., the progression of the patient's seizure disorder, based on the intracranial pressure information. Intracranial pressure information may include, for example, intracranial pressure values sensed by sensing module 66 (FIG. 4) over time or one or more seizure metrics generated by processor 60 (FIG. 4) of IMD 16.

In addition, in some examples, processor 80 may receive patient motion information from motion sensor 67 (FIG. 4) or from a motion sensor that is separate from IMD 16. Processor 80 may evaluate the seizure disorder of patient 12, e.g., the progression of the patient's seizure disorder, based on patient motion information associated with a detected seizure. For example, processor 80 may evaluate the seizure disorder based on the number of convulsive seizures patient 12 experiences, which may be indicated by the patient motion information associated with the detected seizure. As another example, processor 80 may evaluate the seizure disorder based on the number of seizures that resulted in a sudden change in patient posture.

Memory 82 may include instructions for operating user interface 86 and telemetry module 84, and for managing power source 88. Memory 82 may also store any therapy data retrieved from IMD 16 during the course of therapy, as well as seizure data (e.g., seizure indications that indicate the time and date of a seizure), intracranial pressure data, and motion sensor information. The clinician may use this therapy data to determine the progression of the patient condition in order to plan future treatment for the seizure disorder of patient 12. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 88 delivers operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 88 may include circuitry to monitor power remaining within a battery. In this manner, user interface 86 may provide a current battery level indicator or low battery level indicator when the battery needs to be replaced or recharged. In some cases, power source 88 may be capable of estimating the remaining time of operation using the current battery.

Figure 6:
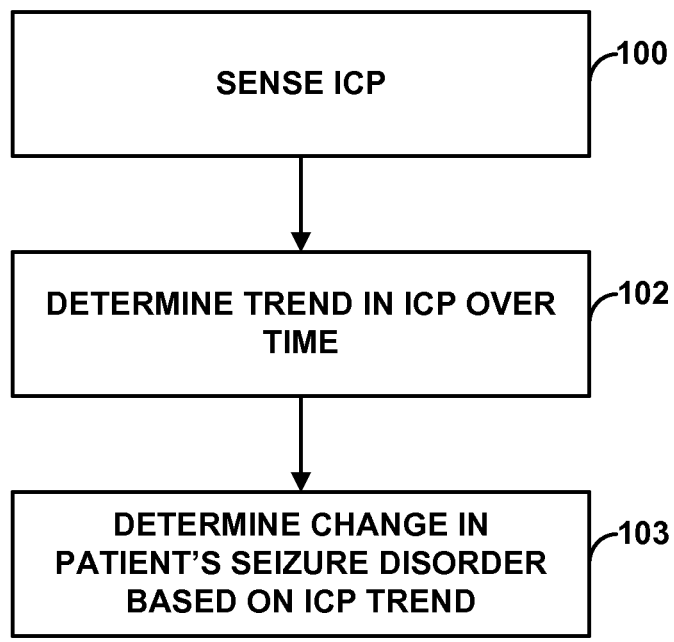
FIG. 6 is a flow diagram of an example technique for monitoring intracranial pressure (ICP) of a patient.

FIG. 6 is a flow diagram illustrating an example technique that processor 60 (FIG. 4) of IMD 16, processor 80 (FIG. 5) of programmer 14, or a processor of another device may implement in order to monitor intracranial pressure of patient 12. Changes in the patient's intracranial pressure over time may indicate that the patient's condition has changed. For example, an increase in intracranial pressure over time may indicate that the status of the patient's seizure disorder has generally changed, e.g., become more severe or changed in terms of the types of seizures patient 12 may be experiencing. In addition, increases in intracranial pressure may be associated with the presence of various physiological conditions, such as neurogenic pulmonary edema, which is a respiratory failure caused, at least in part, by brain swelling. Thus, monitoring for long-term trends in intracranial pressure may be useful for detecting various patient conditions.

A patient condition may be monitored via intracranial pressure alone or in combination with other physiological parameters, such as bioelectrical brain signals, cardiac activity (e.g., via an electrogram or electrocardiogram), patient motion (e.g., via motion sensor 67 of IMD 16), respiratory activity, muscle activity (e.g., via an electromyogram), and the like. In addition, intracranial pressure of patient 12 may be monitored, e.g., as IMD 16 delivers therapy to patient 12 to manage a seizure disorder.

In general, intracranial pressure within a particular range (e.g., less than about 15 millimeters of mercury (mmHg)) may be considered acceptable. While intracranial pressure may periodically rise, e.g., in response to a change in the patient's posture or an increase in activity level, the intracranial pressure generally returns to a baseline intracranial pressure value. The baseline intracranial pressure value is an intracranial pressure value of patient 12 when patient 12 is not in an ictal state of a seizure event, and when the effects of the seizure in the post-ictal state have substantially dissipated. For example, the baseline intracranial pressure value may be a steady-state intracranial pressure value.

The baseline intracranial pressure may include, for example, an intracranial pressure sensed at one point in time, an average intracranial pressure over a range of time (e.g., over a seconds, minutes or hours), or a median intracranial pressure over a range of time. An average (or mean) intracranial pressure may be a more useful indicator of the patient's intracranial pressure over time because the average may minimize outlier intracranial pressure values that are attributable to, for example, changes in the patient's posture or activity level unrelated to the occurrence of a seizure. In some examples, the baseline intracranial pressure is adaptive to adjust over time, e.g., as the mean or median pressure value changes, or may be predetermined and reset by a clinician.

A baseline intracranial pressure value that gradually increases over time may indicate that the patient's seizure disorder state is worsening, or at least changing, and, therefore, additional monitoring of patient 12 or adjustments to the patient's therapy regimen may be desirable. In this way, intracranial pressure monitoring by IMD 16 may be useful for long-term monitoring of patient 12, e.g., monitoring of patient 12 over the course of days, months or even years. If the baseline intracranial pressure value exceeds a threshold value, the intracranial pressure information may also indicate that clinician attention to patient 12 is desirable because patient 12 may be at risk for complications from the increased intracranial pressure. The threshold value may be a maximum acceptable intracranial pressure value as selected by a clinician. Thus, while intracranial pressure values above the threshold value may not be harmful to patient 12, the threshold value may indicate the intracranial pressure value at which further evaluation of the patient's seizure disorder.

Monitoring the intracranial pressure over time of patient 12 may be useful for determining whether patient 12 is at risk for SUDEP and, in some cases, detecting when the patient's risk for SUDEP has increased. For example, an increase in the patient's intracranial pressure over time or a chronic elevated (e.g., about 15 mmHg) intracranial pressure may be indicative of an increased risk of SUDEP. While the exact mechanisms by which intracranial pressure may indicate a change in risk of SUDEP for a particular patient 12 are not known, monitoring intracranial pressure over time, e.g., during chronic therapy delivery by therapy system 10, may be useful for monitoring the patient's seizure disorder and detecting changes in the patient's physiology (e.g., intracranial pressure) that may be indicative of changes to the patient's risk of SUDEP.

The technique shown in FIG. 6 is useful for monitoring the patient's intracranial pressure over time to detect changes to the condition of the patient's seizure disorder. While FIG. 6, as well as FIGS. 7-9 and 11-14 are described has being performed by processor 60 of IMD 16, in other examples, processor 80 of programmer 14 or a processor of another device may perform any part of the technique shown in FIG. 6, alone or in combination with processor 60 of IMD 16.

In accordance with the technique shown in FIG. 6, processor 60 of IMD 16 controls sensing module 66 (FIG. 4) to sense the intracranial pressure (ICP) of patient 12 (100). Sensing module 66 may sense intracranial pressure with one or more pressure sensors 25, 27, which are carried by leads 20 and implanted within cranium 32 (FIG. 1) of patient 12. Processor 60 controls sensing module 66 to sense intracranial pressure at any suitable sensing frequency, such as about at least once per second, once per minute, once per hour, once per day, and the like. In some cases, intracranial pressure of patient 12 may not change rapidly, and, thus, a sensing frequency of about one to about ten times per day may be sufficient to monitor long-term trends in the intracranial pressure values. A frequency of about one to about ten times per day may also be useful for conserving power source 72 (FIG. 4) of IMD 16. However, in some examples, it may be desirable to monitor the change in the patient's intracranial pressure over the course of a day, e.g., while patient 12 undergoes a plurality of different movements and postures, and, thus, sensing module 66 may sense intracranial pressure with a higher frequency.

Moreover, as described below, in some examples, it may be desirable to monitor the patient's intracranial pressure at a higher frequency, such as about once per second or once per minute or more, in order to detect changes in intracranial pressure that are associated with detected seizures. In some examples, processor 60 controls sensing module 66 to increase a frequency with which the intracranial pressure of patient 12 is sensed after detecting a seizure. That is, upon detection of a seizure, processor 60 may automatically switch to a higher intracranial pressure sampling rate in order to acquire more useful intracranial pressure information that is associated with the seizure. A lower intracranial pressure sampling rate may then be resumed after a return of the intracranial pressure value to a baseline value is detected or upon expiration of a predetermined post-ictal time period.

Sensing module 66 transmits an electrical signal indicative of the sensed intracranial pressure to processor 60. Processor 60 determines a trend in intracranial pressure over time (102) based on the electrical signal indicative of the sensed intracranial pressure. In some examples, processor 60 controls sensing module 66 to sense intracranial pressure at a relatively high frequency (e.g., about once per second or once per minute) and processor 60 determines a trend by re-sampling the intracranial pressure values post-hoc (e.g., taking every ten to one hundred data points). In other examples, processor 60 controls sensing module 66 to sense intracranial pressure at a relatively low frequency (e.g., about once per hour or once per day) and processor 60 determines a trend based on each of the intracranial pressure values.

In some examples, processor 60 determines whether the long-term trend of the intracranial pressure is increasing over time. As described with respect to FIG. 7, processor 60 may also determine whether the intracranial pressure at one point in time or the trend over time is greater than or equal to a threshold value that is indicative of an acceptable intracranial pressure value.

As another example, processor 60 may determine a change in intracranial pressure over time. In some examples, processor 60 generates an indication if the change in intracranial pressure over time exceeds a threshold value. However, a large change in intracranial pressure over time may be attributable to other factors, such as changes in patient posture or activity level. Thus, in some examples, processor 60 may correlate large changes in intracranial pressure over time (e.g., a change that exceeds a threshold value) with a detected seizure in order to identify intracranial pressure information that is relevant to the patient's seizure disorder. In addition, in some examples, processor 60 stores the intracranial pressure indication in memory 62 of IMD 16 (FIG. 4), memory 82 of programmer 14 (FIG. 5) or a memory of another device.

In some examples, processor 60 transmits the sensed intracranial pressure values to programmer 14 or another computing device via the respective telemetry modules 70 (FIG. 4), 84 (FIG. 5). Processor 80 of programmer 14 may, for example, generate a graphical display of the intracranial pressure of patient 12 over time and present the display to a user (e.g., a clinician or patient 12) via a display of user interface 86.

Processor 60 or processor 80 or a clinician with the aid of one or both processors 60, 80 determine a change in the patient's seizure disorder based on the trend in the intracranial pressure values (103). For example, processor 60, 80 may determine that the patient's seizure disorder is changing, e.g., becoming worse, if the trend indicates the patient's intracranial pressure value is increasing over time or increases beyond a particular value.

Figure 7:
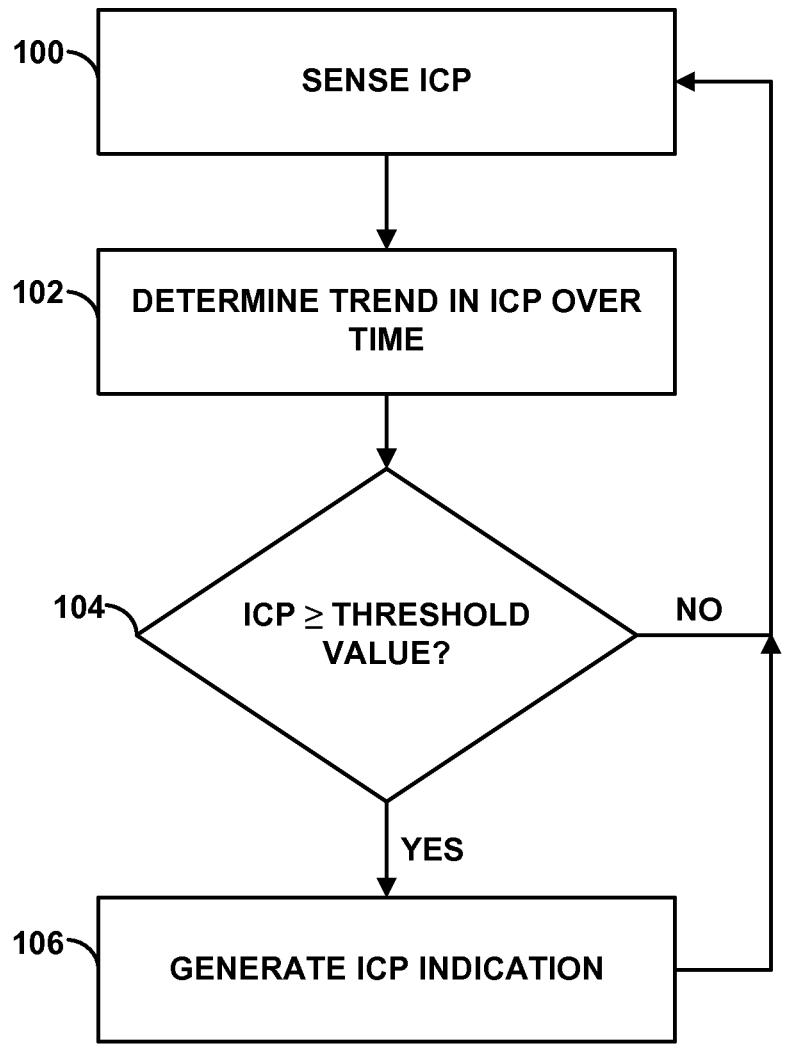
FIG. 7 is a flow diagram of another example technique for monitoring intracranial pressure of a patient and generating an indication if the intracranial pressure exceeds a threshold value.

FIG. 7 is a flow diagram of another example technique that processor 60 may implement in order to monitor intracranial pressure of patient 12 over time. Processor 60 controls sensing module 66 (FIG. 4) to sense the intracranial pressure of patient 12 (100). Processor 60 determines a trend in the intracranial pressure over time (102). Processor 60 periodically determines whether an intracranial pressure value is greater than or equal to a threshold value (104). In some examples, processor 60 determines whether the most recently determined intracranial pressure value, which may be a mean or median intracranial pressure value, is greater than or equal to the threshold value (104). In this way, processor 60 may determine whether the patient's baseline intracranial pressure has increased over time to an unacceptably high level.

The threshold value may indicate a maximum, acceptable intracranial pressure value. As previously indicated, an intracranial pressure value greater than or equal to the threshold value may not be harmful to patient 12, but may merely indicate that clinician attention is desirable and/or the intracranial pressure greater than or equal to the threshold value is a physiological event worth designating. While the threshold value may differ between patients, in some examples, the threshold value may be about 12 mmHg to about 20 mmHg, such as about 15 mmHg. In healthy patients, a baseline intracranial pressure value may remain between about 1 mmHg to about 15 mmHg, although the intracranial pressure may periodically increase to 20 mmHg or greater depending on patient posture or activity level. In addition, intracranial pressure may be negative in some examples, such as when patient 12 is in particular postures. Thus, the baseline intracranial pressure value may be less than zero mmHg in some examples.

If the intracranial pressure value is not greater than or equal to the threshold value (104), processor 60 continues monitoring intracranial pressure (100) and determining the trend of the intracranial pressure over time (102). On the other hand, if the intracranial pressure value is greater than or equal to the threshold value (104), processor 60 generates an intracranial pressure indication (106). The intracranial pressure indication may be, for example, a flag, value or another signal stored in memory 62 (FIG. 4) of IMD 16 or transmitted to programmer 14 and stored in memory 82 of programmer 14. The intracranial pressure indication may indicate that an intracranial pressure value that exceeds an identified acceptable range (as indicated by the threshold value), which may be selected by the clinician, was observed. The intracranial pressure indication may be stored as seizure and intracranial pressure information 76 (FIG. 4) in memory 62 of IMD 16, and may also include a date and time stamp. A clinician may later retrieve the intracranial pressure indication to evaluate the status of the patient's seizure disorder.

In some examples, processor 60 of IMD 16 or processor 80 of programmer 14 may monitor the intracranial pressure of patient 12 over time using the technique shown in FIG. 7 in order to identify when patient 12 may need treatment. For example, processor 60 of IMD 16 or processor 80 of programmer 14 may determine that patient 12 needs to seek clinician attention when a sensed intracranial pressure is greater than or equal to a threshold value. Thus, in some examples, processor 60 or 80 generates a notification upon the generation of the intracranial pressure indication. The notification may be used to alert patient 12 or a caregiver that clinician attention is desirable and/or alert the clinician that the intracranial pressure of patient 12 indicates analysis and/or further treatment of patient 12 may be desirable. In some examples, processor 60 of IMD 16 generates the alert by generating a somatosensory alert, such as by vibrating in a manner that patient 12 recognizes as the notification. Processor 80 of programmer 14 may generate the notification via a visual or auditory alert transmitted to patient 12 or the clinician via user interface 86 (FIG. 5), or via a somatosensory alert (e.g., pulsed vibrations). The intracranial pressure indication may be transmitted to a remote location (e.g., a clinician's office) via any suitable wired or wireless network.

Figure 8:
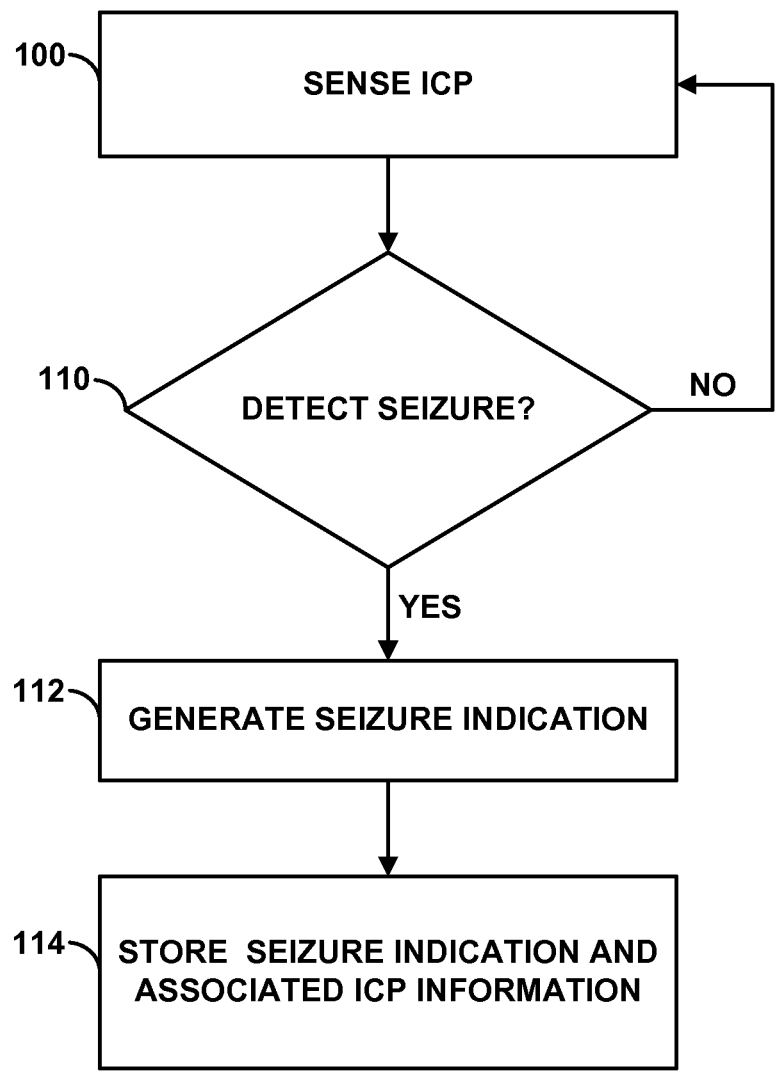
FIG. 8 is a flow diagram of an example technique for associating a detected seizure with intracranial pressure information.

FIG. 8 is a flow diagram of an example technique for associating detected seizures based on intracranial pressure information. Processor 60 of IMD 16 controls sensing module 66 (FIG. 4) to sense intracranial pressure of patient 12 via one or more pressure sensors 25, 27 (FIG. 4) implanted within cranium 32 (FIG. 1) of patient 12 (100). Processor 60 detects a seizure (110) using any suitable technique. In some examples, processor 60 detects the seizure based on bioelectrical brain signals of patient 12, or impedance of brain tissue of patient 12, as described above. In other examples, processor 60 detects a seizure based on input from patient 12 or a patient caretaker. For example, after the onset of a seizure, patient 12 or the caretaker may provide input via programmer 14 or IMD 16 (e.g., by tapping IMD 16 in a predetermined pattern, and IMD 16 may include a motion detector to detect the patient input) to indicate a seizure occurred. The input may also indicate a time frame in which the seizure occurred (e.g., an hour ago, a day ago, etc.).

If processor 60 does not detect the seizure, processor 60 continues monitoring intracranial pressure of patient (100). If processor 60 detects a seizure (110), processor 60 generates a seizure indication (112). The seizure indication may be a flag, value or another signal stored in memory 62 of IMD 16 or a memory of another device (e.g., programmer 14) to indicate the occurrence of a seizure. In some examples, the seizure indication may be stored in memory 62 with a date and time stamp to indicate the time at which the seizure was detected. Processor 60 stores the seizure indication and associated intracranial pressure information in memory 62 (114) or transmits the seizure indication and associated intracranial pressure information to another device, such as programmer 14. The intracranial pressure information associated with the seizure indication may include, for example, the signals from pressure sensors 25, 27 that correspond in time to the detected seizure. For example, signals indicative of intracranial pressure during a pre-ictal, ictal, and post-ictal state, or any combination thereof, may be stored in memory 62.

In some examples, the intracranial pressure information associated with the seizure indication may include one or more seizure metrics generated based on the pressure sensed by pressure sensors 25, 27. Processor 60 of IMD 16 or a processor of another device (e.g., programmer 14) may determine a seizure metric for each detected seizure of patient 12 based on sensed intracranial pressure of patient 12 associated with the seizure indication. The seizure metrics may be determined based on intracranial pressure values of patient 12 determined at any suitable frequency, such as a sampling frequency of about once per second, once per minute, or at a higher or lower frequency.

As previously indicated, the seizure metrics may be useful for monitoring the patient's seizures, monitoring the progression of the patient's seizure disorder, and distinguishing between different seizures detected by IMD 16. Processor 60 of IMD 16 or processor 80 of programmer 14 may determine a seizure metric associated with the detected seizure based on the intracranial pressure sensed during the seizure, and, in some cases, before and after the seizure. In some examples, the seizure metric may indicate the relative level of intracranial pressure (e.g., based on a preset categorization of intracranial pressure, such as normal, elevated, and high intracranial pressure), a highest intracranial pressure value observed during an ictal state of the seizure, a percent change from a baseline intracranial pressure value, an amount of time it took for the patient's intracranial pressure to return to a baseline value, a standard deviation of the intracranial pressure from the baseline value during the ictal state, or a change in the intracranial pressure values over time during the ictal state.

In some examples, processor 60 also stores a bioelectrical brain signal (e.g., EEG or ECoG signals) in memory 62 along with the seizure indication and associated intracranial pressure information. The bioelectrical brain signal that temporally correlates to the intracranial pressure signal may be useful for analyzing the seizure. In addition, in some examples, storing the bioelectrical brain signal may also permit a clinician to determine when a seizure was detected, and, therefore, the intracranial pressure signals from sensing module 66 (FIG. 4) of IMD 16 that correspond to the detected seizure.

In addition, in some examples, processor 60 also stores a signals from motion sensor 67 (FIG. 4) in memory 62 along with the seizure indication and associated intracranial pressure information and, in some cases, bioelectrical brain signals. The motion sensor signal that temporally correlates to the intracranial pressure signal may be useful for analyzing the seizure. For example, as previously discussed, the motion sensor signal may be used to determine whether a seizure detected based on a bioelectrical brain signal is associated with a motor component or was merely a sensory seizure.

Figure 9:
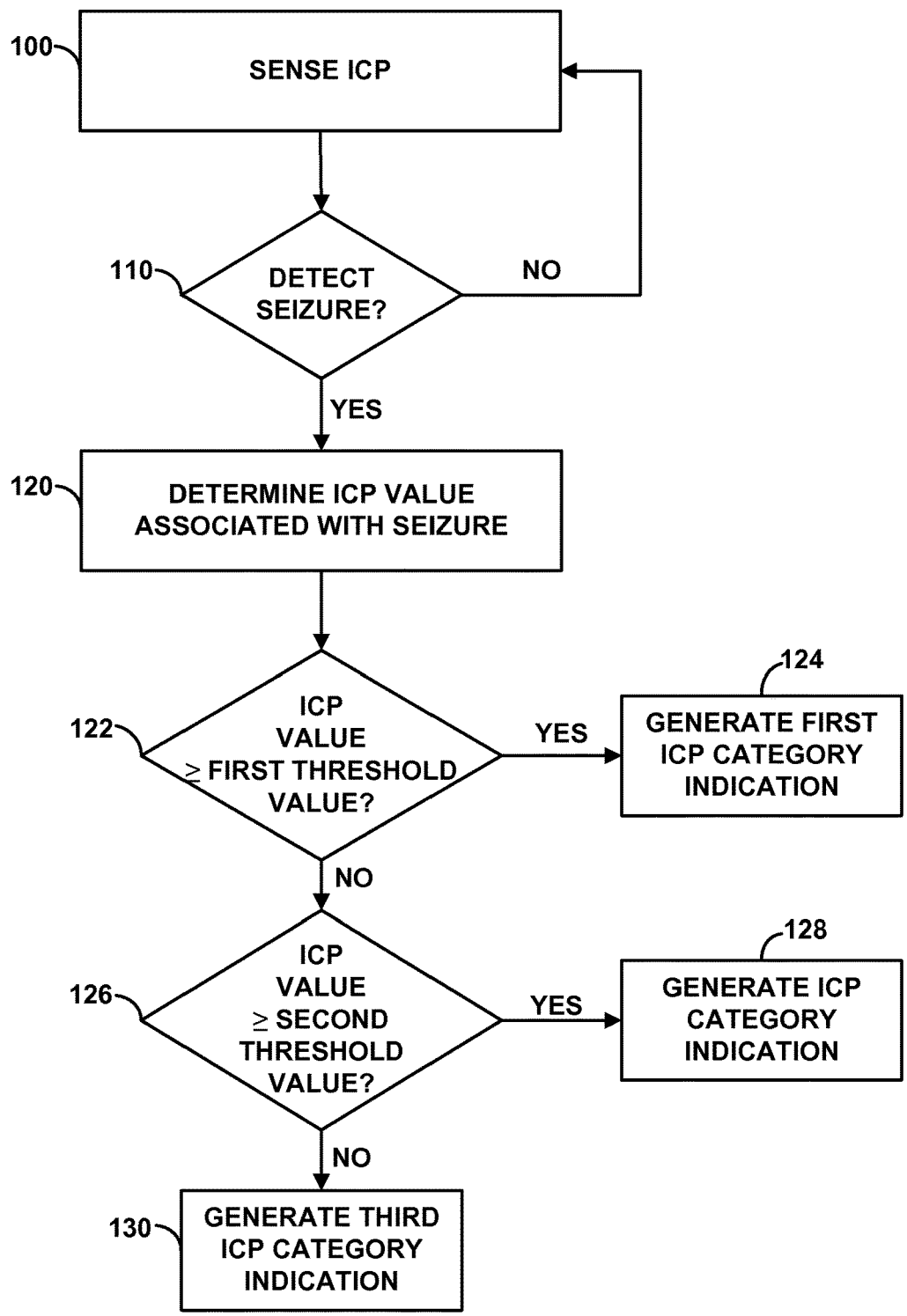
FIG. 9 is a flow diagram of an example technique for determining a seizure metric that indicates an intracranial pressure category associated with a seizure.

FIG. 9 is a flow diagram that processor 60 of IMD 16 may implement in order to determine a seizure metric associated with a detected seizure. In the example shown in FIG. 9, the seizure metric is a relative level of intracranial pressure associated with a detected seizure, as indicated by different categories. In accordance with the technique shown in FIG. 9, processor 60 of IMD 16 monitors intracranial pressure (ICP) of patient 12 via sensing module 66 (FIG. 4) (100). Processor 60 detects a seizure (110), as described above with respect to FIG. 8. Processor 60 also determines an intracranial pressure value associated with the seizure (120). In some examples, the intracranial pressure value may be a mean or median intracranial pressure value during an ictal state of the seizure. In other examples, the intracranial pressure value may be a highest intracranial pressure value observed during the ictal state of the seizure. The ictal state of the seizure may be determined based on a bioelectrical brain signal (e.g., an ECoG signal or EEG signal). Processor 60 may begin monitoring the intracranial pressure prior to the detection of the seizure, during the detection of the seizure or after the detection of the seizure.

In the technique shown in FIG. 9, processor 60 compares the intracranial pressure value associated with the seizure to a first threshold value (122). In the example shown in FIG. 9, the first threshold value indicates a high intracranial pressure, which may be within an undesirable range of intracranial pressure values. In some examples, the first threshold value may be about 20 mmHg or higher. If the intracranial pressure value associated with the seizure is greater than or equal to the first threshold value (122), processor 60 generates a first intracranial pressure (ICP) category indication (124). The first intracranial pressure indication may be associated with the seizure in memory 62 of IMD 16 or a memory of another device (e.g., programmer 14). The first intracranial pressure category indication may indicate, for example, that the seizure was associated with a high intracranial pressure. A seizure associated with the first intracranial pressure category indication may be indicative of a relatively severe seizure.

If the intracranial pressure value associated with the seizure is not greater than or equal to the first threshold value (122), processor 60 determines whether the intracranial pressure value is greater than or equal to a second threshold value (126). In the example shown in FIG. 9, the second threshold value is a value indicative of an elevated intracranial pressure, which may be within acceptable intracranial pressure limits, but not considered normal, e.g., considered outside the range of intracranial pressure values for a healthy patient. In some examples, the second threshold value may be about 15 mmHg to less than about 20 mmHg. If the intracranial pressure value associated with the seizure is greater than or equal to the second threshold value (126), processor 60 generates a second intracranial pressure category indication (128). The second intracranial pressure category indication may be associated with the seizure in memory 62 of IMD 16 or a memory of another device (e.g., programmer 14). The second intracranial pressure category indication may indicate, for example, that the seizure was associated with an elevated intracranial pressure, but was within acceptable limits.

If the intracranial pressure value associated with the seizure is not greater than or equal to the second threshold value (126), processor 60 generates a third intracranial pressure category indication (130). The third intracranial pressure category indication may indicate, for example, that the seizure was associated with a normal range of intracranial pressure values, rather than an elevated intracranial pressure values.

Processor 60 or a clinician with the aid of a computing device (e.g., programmer 14) may use the intracranial pressure category indications, as well as other types of seizure metrics associated with the seizures to distinguish between the seizures that patient 12 experiences. For example, a clinician may determine that information relating to the seizures associated with the first and second intracranial pressure category indications, e.g., which in the example shown in FIG. 9 are seizures associated with a higher than normal intracranial pressure, is useful for evaluating the patient's seizure disorder. In some cases, the seizures associated with the higher than normal intracranial pressure may be more useful for evaluating the patient's seizure disorder status than seizures associated with a normal intracranial pressure because the higher than normal intracranial pressures may indicate a change in the patient's seizure disorder status. Thus, in the example shown in FIG. 9, processor 60 of IMD 16 or processor 80 of programmer 14 may filter out the seizures associated with the first and second seizure metrics and present a list of such seizures and associated intracranial pressure values to the clinician via a display of user interface 86 (FIG. 5) of programmer 14. The values for the higher than normal intracranial pressure and normal intracranial pressure may be determined based on observations specific to patient 12 or to a class of patients.

The number of seizures associated with a first seizure metric and, in some cases, the second seizure metric, may be indicative of a change in the patient's seizure disorder, such as a progression of the seizure disorder. For example, the number of occurrences of seizures associated with a first seizure metric and, in some cases, the second seizure metric, may be revealing of an increased risk of SUDEP.

FIG. 10 is an example data structure that processor 80 of programmer 14 may generate and present to a user via a display of user interface 88 (FIG. 5). Although FIG. 10 illustrates a table, programmer 14 may also present seizure and intracranial pressure information via any suitable data structure.

The table shown in FIG. 10 lists a plurality of detected seizures ("SEIZURE 1," "SEIZURE 2," etc.), and seizure metrics associated with each detected seizure. In FIG. 10 "N" number of seizures are listed. In the example shown in FIG. 10, the seizure metrics include an intracranial pressure category ("NORMAL," "ELEVATED," AND "HIGH"). FIG. 9 describes a technique for determining an intracranial pressure category for a detected seizure. The seizure metrics included in the table of FIG. 10 also include a percent change of the intracranial pressure value during the seizure relative to a baseline intracranial pressure, a highest intracranial pressure value sensed during the ictal state of the seizure, and a time required to return to a baseline intracranial pressure value, e.g., after the occurrence of the seizure. Other seizure metrics may include a standard deviation of the intracranial pressure from the baseline value during the ictal state or a change in the intracranial pressure values over time during the ictal state.

Processor 60 of IMD 16 or processor 80 of programmer 14 may determine the percent change of the intracranial pressure during the seizure relative to a baseline intracranial pressure value using any suitable technique. In one example, the intracranial pressure value used to determine the percent change relative to the baseline intracranial pressure value may be a mean, median or highest intracranial pressure value during the ictal state of the seizure. In other example, the intracranial pressure value used to determine the percent change from the baseline intracranial pressure value may be randomly selected during the ictal state of the seizure. In some examples, all data samples are used for computing the intracranial pressure value for determining the percent change from the baseline. In other examples, the intracranial pressure value may be derived from randomly selected values during the ictal state of the seizure.

The baseline intracranial pressure value may be determine using any suitable technique, and may be stored in memory 62 of IMD 16 or memory 82 of programmer 14. In some examples, the baseline intracranial pressure value may be the mean or median intracranial pressure value during a time period preceding the detection of the seizure. For example, the intracranial pressure value may be the mean or median intracranial pressure value of the intracranial pressure values sensed (e.g., in accordance with the technique shown in FIG. 6) for about one hour to about one week prior to the detection of the seizure. In this way, the baseline intracranial pressure value may be a dynamic value that is periodically updated. In other examples, the baseline intracranial pressure value may be preset and may not be dynamically changed. For example, the baseline intracranial pressure value may be the intracranial pressure value when therapy system 10 is implanted within patient 12, or at some time at some time prior to the implementation of therapy system 10. As another example, the baseline intracranial pressure value may be selected by a clinician, and may be, for example, an average intracranial pressure value for a patient that does not have a seizure disorder.

Figure 11:
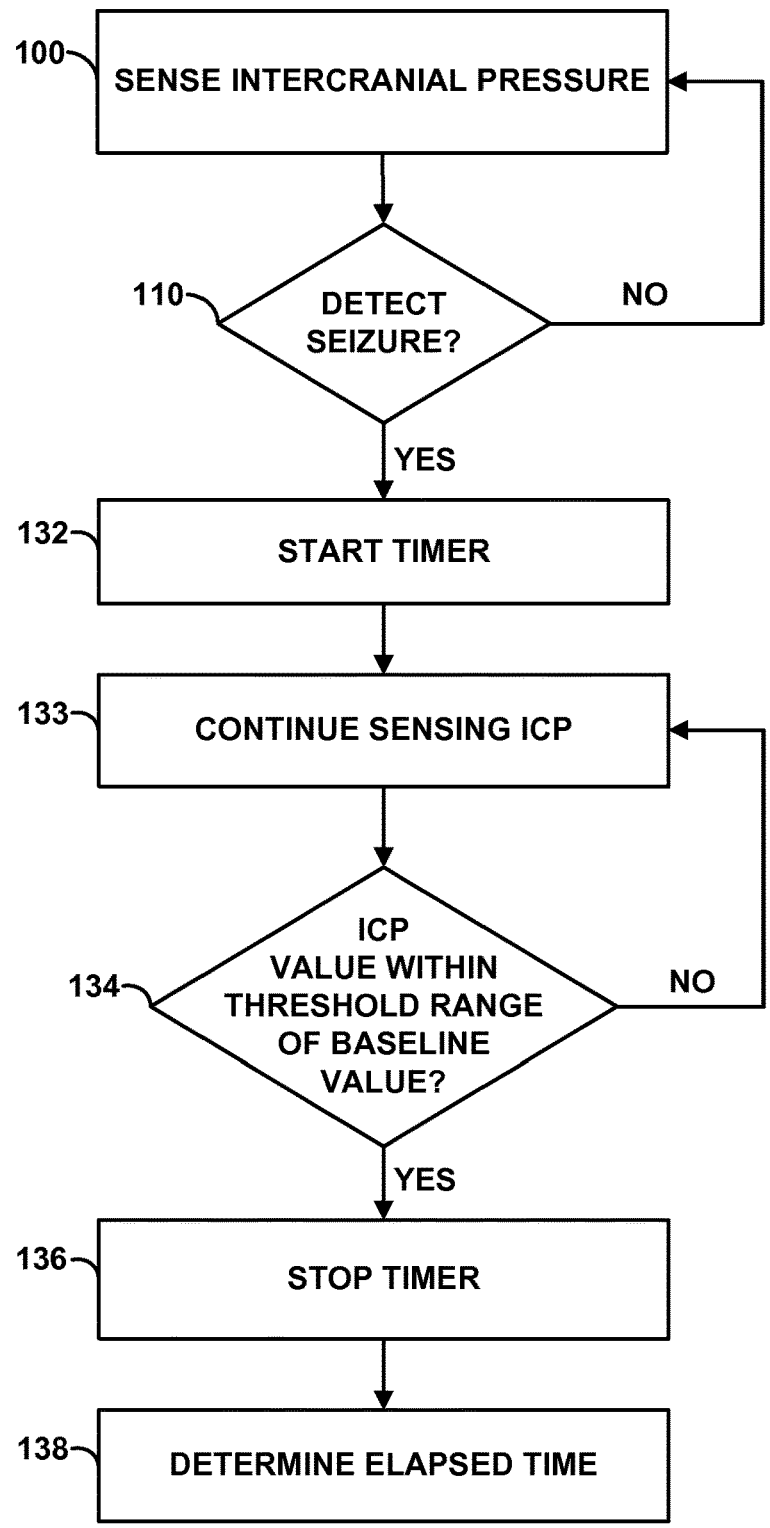
FIG. 11 is a flow diagram of an example technique for determining a seizure metric that indicates a duration of time required for an intracranial pressure of a patient to return to a baseline value after the detection of a seizure.

Processor 60 of IMD 16 or processor 80 of programmer 14 may determine the seizure metric that indicates the time required for the intracranial pressure of patient 12 to return to a baseline value following the detection of a seizure using any suitable technique. An example technique for determining the time required for the intracranial pressure to return to a baseline value is illustrated in FIG. 11. As shown in FIG. 11, processor 60 of IMD 16 controls sensing module 66 (FIG. 4) to sense intracranial pressure of patient 12 (100). Upon detection of a seizure (110), processor 60 starts a timer (132) in order to track the amount of time required for the intracranial pressure of patient 12 to return to a baseline value following the detection of a seizure.

Sensing module 66 may continue sensing intracranial pressure and processor 60 may continue monitoring intracranial pressure (133). After detection of the seizure, processor 60 compares the intracranial pressure of patient 12 to a baseline value (134). In particular, in the example shown in FIG. 11, processor 60 determines whether the current (e.g., real-time) intracranial pressure of patient 12 sensed after detection of the seizure is within a threshold range of a baseline value (134). The baseline value may be stored in memory 62 of IMD 16, memory 82 of programmer 14 or a memory of another device. As indicated above, the baseline value may be preset or may be the mean or median intracranial pressure value of the intracranial pressure values sensed during a time period preceding the detection of the seizure (110).

In some cases, the intracranial pressure of patient 12 sensed after detection of the seizure may be sensed during the seizure. That is, depending upon the duration of a seizure, processor 60 may begin comparing the intracranial pressure of patient 12 to a baseline value (134) while the seizure is still occurring, e.g., during the ictal state of the seizure.

If processor 60 determines that the current (e.g., real-time) intracranial pressure of patient 12 sensed after detection of the seizure is within a threshold range of a baseline value (134), processor 60 stops the timer (136) and determines how much time has elapsed since the seizure was detected based on the duration of time indicated by the timer (138). The elapsed time may indicate the time required for the intracranial pressure of patient 12 to return to a baseline value following a detection of a seizure. The elapsed time may be stored as a seizure metric in memory 62 (FIG. 4) of IMD 16.

The threshold range may be determined by a clinician and stored in IMD 16 or programmer 14. In some examples, the threshold range may be defined in terms of a percent of the baseline value. For example, the threshold range may be about 75% to about 125% of the baseline value, such that an intracranial pressure value that is about 75% to about 125% of the baseline value may indicate the intracranial pressure returned to the threshold range of the baseline value. In other examples, the threshold range may be defined in terms of absolute intracranial pressure values. For example, the threshold range may be about 0 mmHg to about 3 mmHg of the baseline intracranial pressure value. Any suitable threshold ranges are contemplated.

The threshold range that indicates the intracranial pressure of patient 12 is within an acceptable range of the baseline value may be specific to patient 12, e.g., based on the patient's baseline intracranial pressure value, or may be applicable to more than one patient. For example, with patients that have a relatively high baseline intracranial pressure value, the threshold range may be relatively small because a smaller increase in intracranial pressure may result in an intracranial pressure value that is undesirably high (e.g., about 15 mmHg or above 20 mmHg). On the other hand, patients that have a relatively low baseline intracranial pressure value may be associated with a relatively large threshold range.

If processor 60 determines that the current intracranial pressure of patient 12 sensed after detection of the seizure is not within the threshold range of the baseline value (134), processor 60 continues monitoring the intracranial pressure until the intracranial pressure is within the threshold range of the baseline value.

In other examples, processor 60 determines the amount of time that elapsed between the end of a seizure (e.g., the end of the ictal state) and the time at which the intracranial pressure of patient 12 returned to the baseline value. Processor 60 detects the end of a seizure using any suitable technique. In some examples, processor 60 detects the end of a seizure based on a bioelectrical brain signal of patient 12, e.g., using techniques similar to those used to detect the seizure. In other examples, processor 60 receives input from patient 12 or another user (e.g., a patient caretaker) via programmer 14 that indicates the seizure has terminated.

Returning now to FIG. 10, in some examples, the data structure that presents the seizure and intracranial pressure information (e.g., seizure metrics) to a user may also include a seizure severity rating. The seizure severity rating may be based on subjective input from a user, and/or the seizure metrics that are based on intracranial pressure of patient 12 sensed upon the detection of the seizure. In some examples, the subjective input from the user rating the severity of the seizure may be provided via user interface 86 (FIG. 5) of programmer 14. With the aid of programmer 14, a user may assign a numeric rating to a seizure (e.g., on a scale of 1 to 5, where a level '5" may indicate a severe seizure and a level "1" may indicate a relatively minor seizure), as shown in FIG. 10, or assign a textual rating to a seizure (e.g., via indicators, such as "MINOR," "MODERATE," "SEVERE," and the like).

In some examples, the severity of the patient's seizure may be automatically detected based on one or more a monitored physiological parameters values of patient 12, such as an EEG signal, an ECG signal or intracranial pressure, e.g., as indicated by the seizure metrics. As previously described, IMD 16 or another sensing device may monitor one or more physiological parameters of patient 12. In some examples, processor 60 of IMD 16 or processor 80 of programmer 14 may automatically determine the severity of the seizure based on, for example, the amplitude of a bioelectrical signal waveform. Processor 80 of programmer 14 or a processor of another device (e.g., IMD 16) may determine the severity of the seizure and automatically record the severity within memory 82 of programmer 14 or memory 62 of IMD 16. Severity may be categorized in terms of a graduated scale (e.g., a numerical scale) or another suitable scale. Alternatively, processor 60 or 80 may merely record the EEG signal and clinician or another computing device may determine the severity of the patient's seizure, if any, at the time the event marker was generated.

In some examples, the severity of the seizure may be automatically determined based on a seizure metric. For example, if a seizure is associated with a particular intracranial pressure category (shown in FIG. 10 as "ICP CATEGORY"), such as "ELEVATED" or "HIGH," processor 60 of IMD 16 or processor 80 of programmer 14 may automatically categorize the seizure as a severe seizure. As another example, if the percent change of the intracranial pressure of patient 12 relative to a baseline value is relatively large (e.g., greater than or equal to about 50%), processor 60 and/or 80 may automatically categorize the seizure as a severe seizure. Subcategories of severe seizures may also be used, such as "moderately severe," "extremely severe," and the like.

As described in further detail below with reference to FIGS. 12 and 13, IMD 16 may also monitor the patient's activity level and determine a type of seizure (e.g., convulsive or nonconvulsive, or sensory seizure or motor seizure) and/or a severity of a seizure based on the patient's activity level during the seizure. In some examples, processor 60 or 80 may determine that a detected seizure was severe if the seizure was associated with a relatively high activity level (e.g., indicating a convulsive seizure or a motor seizure) or associated with a sudden change in posture (e.g., indicating a fall).

In some examples, the data structure shown in FIG. 10, which may be presented to a user via programmer 14, may also indicate the type of seizure (not shown in FIG. 10). For example, the user may identify the type of seizure via programmer 14. Processor 80 of programmer 14 may present a list of seizure types, which may be categorized by the extent to which they affect the brain, the affect on a patient's consciousness, and the behavioral effects. For example, a partial seizure affects only a localized area of the brain, while a generalized seizure affects both hemispheres of the brain. Each of these major categories may be further broken up into a number of sub-categories such as, for example, simple partial seizures, complex partial seizures, absence seizures, tonic-clonic seizures, and the like. Thus, in some examples, processor 80 of programmer 14 may present a list of seizure type to a user, where the seizure types includes simple partial seizures, complex partial seizures, absence seizures, and tonic-clonic seizures, and the user may interact with user interface 86 (FIG. 5) of programmer 14 to select a seizure type.

In some examples, the seizure disorder of patient 12 may be evaluated based on a patient activity level or a patient posture that is associated with a respective detected seizure. As described in further detail below, the patient activity level or patient posture level sensed after the detection of a seizure may indicate the type of seizure or the severity of the seizure. For example, a relatively severe seizure, such as a tonic-clonic seizure, may result in involuntary patient movement, e.g., in the form of convulsive muscle movement. In contrast, a relatively minor seizure may not have a motor component, such that patient 12 does not undergo any characteristic movements during the seizure. In addition, a relatively severe seizure may result in a fall or another sudden change in posture by patient 12. Thus, detecting patient posture or patient activity level may be useful for identifying relatively severe seizures.

The patient activity level and patient posture may be monitored via motion sensor 67 (FIG. 4), which may be included in a common housing with the components of IMD 16, and/or a motion sensor carried by a therapy delivery element (e.g., leads 20 of FIG. 1 or catheter 54 of FIG. 3) connected to IMD 16, attached to an outer housing of IMD 16, or physically separate from IMD 16. In examples in which the motion sensor is physically separate from IMD 16, the motion sensor may be external or implanted within patient 12. As described above, in some examples, a device separate from IMD 16 and therapy delivery elements may include both a pressure sensor for sensing intracranial pressure and a motion sensor.

In some examples, a lead including one or more electrical stimulation electrodes and pressure sensors may also include one or more motion sensors (e.g., accelerometers or piezoelectric crystals) that detect patient movement or posture. The motion sensors, electrodes, and pressure sensors may have any suitable arrangement relative to each other. For example, a motion sensor may be positioned between a pressure sensor and electrode, between electrodes, between pressure sensors, distal to one or more electrodes, proximal to one or more electrodes, proximal to one or more pressure sensors, distal to one or more pressure sensors, and the like.

If a motion sensor is disposed on a therapy delivery element that is connected to IMD 16, IMD 16 may also include a motion sensor. The relative motion between the therapy delivery element and housing of IMD 16 may be detected based on the signals from both motion sensors. In this way, certain patient postures or changes in patient postures may also be discerned based on signals from the motion sensors. In some examples, patient motion may also be detected via an electromyography sensor that generates an electrical signal indicative of muscle movement.

A motion sensor may generate a signal indicative of patient motion or posture. For example, when the motion sensor is positioned within cranium 32 (FIG. 3) of patient 12, the motion sensor may generate an electrical signal indicative of movement of the patient's head. For some patients, certain types of seizures may result in a pulling action of the patient's head. Thus, the motion sensor may be used to detect seizures that include such pulling action. As another example, when the motion sensor is positioned within cranium 32 of patient 12 or within IMD 16, which may not be implanted within cranium 32 but within the patient's torso, the motion sensor may generate an electrical signal indicative of convulsive motion of patient 12. For some patients, certain types of seizures (e.g., a tonic-clonic seizure) may result in the patient undergoing involuntary, convulsive movement. The convulsive movement may include, for example, twitching or violent shaking of the arms and legs. It may be desirable to monitor the patient's activity level during a seizure to detect seizures in which convulsive movement or other involuntary movement of patient 12 is observed.

Figure 12:
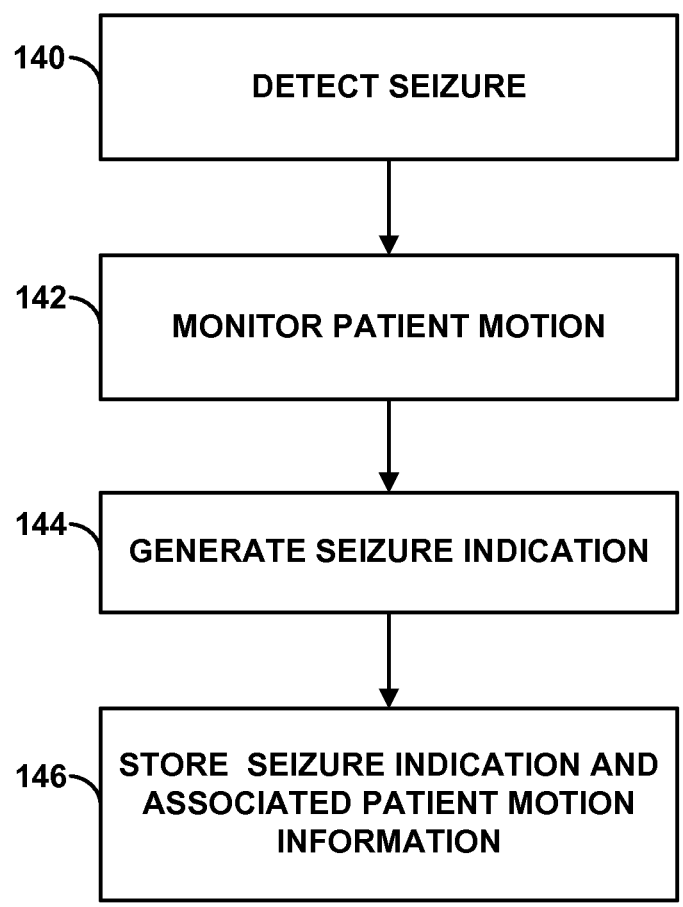
FIG. 12 is a flow diagram of an example technique for associating a detected seizure with patient motion information.
Figure 13:
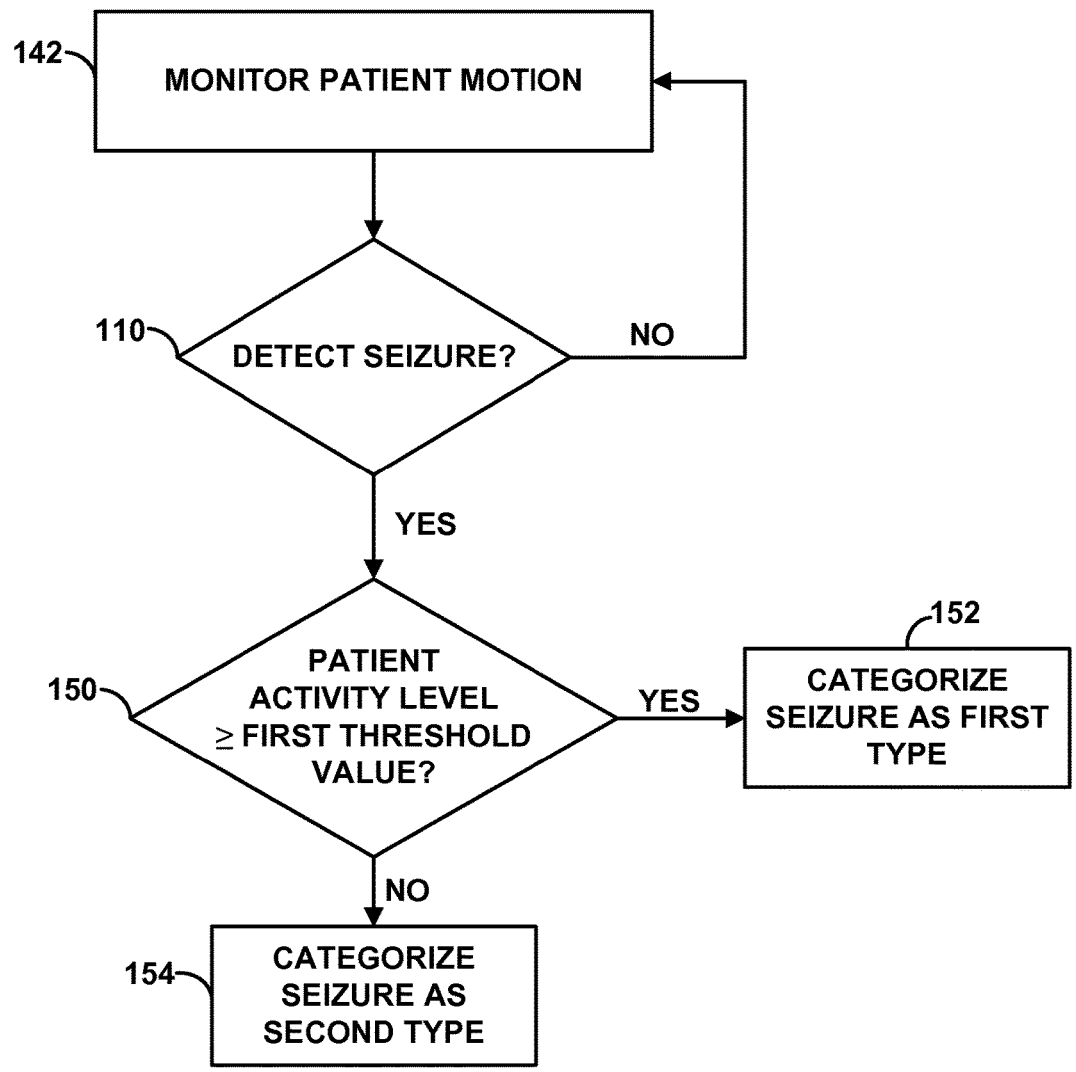
FIG. 13 is a flow diagram of an example technique for generating a seizure metric that indicates a type of seizure.

While motion sensor 67 of IMD 16 is referred to throughout the description of FIGS. 12 and 13, in other examples, motion sensors separate from IMD 16, e.g., carried by a therapy delivery element, may be used to detect patient movement.

FIG. 12 is a flow diagram illustrating an example technique for determining a patient activity level or posture level associated with a detected seizure. Processor 60 of IMD 16 detects a seizure (140), e.g., using the techniques described above with respect to FIG. 8. Processor 60 monitors the patient motion (142), e.g., by receiving an electrical signal generated by motion sensor 67. In some examples, processor 60 may monitor patient motion prior to the seizure in addition to the ictal and post-ictal states associated with the seizure. In other examples, however, processor 60 beings monitoring patient motion after the detection of the seizure. Characteristics (e.g., amplitude or frequency) of the electrical signal output by motion sensor 67 may vary based on patient motion.

In the example shown in FIG. 12, processor 60 generates a seizure indication (144) after detecting the seizure, where the seizure indication may indicate the occurrence of a seizure, and, in some examples, the date and time the seizure was detected. Processor 60 stores the seizure indication and associated patient motion information in memory 62 of IMD 16 (FIG. 4) or a memory of another device, such as programmer 14 (146). The patient motion information may include, for example, the electrical signal from motion sensor 67 that corresponds in time to the detected seizure, or specific patient postures or other patient posture or activity level parameters determined based on the electrical signal from motion sensor 67 of IMD 16. The patient motion information may indicate the motion or posture of patient 12 during the pre-ictal, ictal, and post-ictal states. The patient motion information provides the clinician with an understanding of the change in the patient's posture or activity level during the seizure, as compared to the patient's posture or activity level prior to the seizure and after the seizure.

The patient motion information may be used to distinguish detected seizures from each other. For example, processor 60 of IMD 16, processor 80 (FIG. 5) of programmer 14, a processor of another device may automatically filter out seizures that are associated with a particular level of patient motion that is determined based on the patient motion information.

A clinician may determine that, for example, seizures associated with convulsive motion, a relatively fast change in activity level, or a relatively fast change in posture, which may indicate patient 12 fell as a result of the seizure, are useful for evaluating the seizure disorder status of patient 12. For example, the number of seizures associated with convulsive motion or a sudden change in posture, or a change in the number of such seizures over time may indicate the seizure disorder of patient 12 is changing, and, in some cases, worsening. Thus, motion sensor 67 may be useful for monitoring the patient's seizure disorder status. In some cases, processor 60 of IMD 16 or processor 80 of programmer 14 may receive an electrical signal from motion sensor 67 and correlate the signal with a bioelectrical brain signal to determine the patient motion associated with a seizure. In this way, sensing module 66 (FIG. 4) of IMD 16 may be used to detect a seizure and determine the patient motion information that is relevant to the detected seizure.

Convulsive motion, e.g., an increase in activity level or a motion having a particular pattern, may be detected using any suitable technique. The algorithms implemented by processor 60 of IMD 16 or processor 80 of programmer 14 to detect convulsive motion, as well as to detect sudden changes in patient posture that indicate patient 12 may have fallen as a result of a seizure, may be configured to discriminate convulsive motion from normal patient movements, e.g., movements incident to daily activities of patient 12 when patient 12 is not seizing. Memory 62 of IMD 16 or memory 82 of programmer 14 may store one or more templates or threshold values (e.g., slope values) for detecting convulsive motion based on a signal generated by motion sensor 67.

A clinician may also determine that, for example, seizures associated with an increased level of motion, a abnormal change in activity level indicates the detected seizure was a motor seizure. That is, processor 60 may determine that seizures detected based on bioelectrical brain signals of patient 12 and a change in motion are motor seizures. Processor 60 may also determine that seizures detected based on bioelectrical brain signals of patient 12 not associated with a change in motion are sensor seizures. Distinguishing between motor and sensory seizures may be useful for evaluating the patient's seizure disorder status. For example, a change in the relative number of motor and sensory seizures may indicate a change in the patient's seizure disorder, which may merit an analysis of the therapy system implemented to manage the patient's seizure disorder.

In some examples, processor 60 of IMD 16 or processor 80 of programmer 14 determines whether the output from motion sensor 67 indicates a particular patient posture or activity level (e.g., a convulsive state) by comparing a signal from motion sensor 67 with a stored template or threshold value (e.g., a threshold amplitude value). For example, processor 60 or 80 may compare an amplitude of the electrical signal generated by motion sensor 67 within a certain period of time following the detection of the seizure with a threshold value. The period of time may be selected to be an average duration of a seizure for patient 12 or for a class of patients with similar seizure disorders. The amplitude may be, for example, an instantaneous, mean, median or highest relative amplitude of the electrical signal generated by motion sensor 67. The threshold value may be stored in IMD 16 or programmer 14.

If the mean, median or highest relative amplitude of the electrical signal generated by the motion sensor is greater than or equal to the threshold value, processor 60 or 80 may determine that the patient activity level associated with the seizure is relatively high and, therefore, indicates convulsive motion. On the other hand, if the mean, median or highest relative amplitude of the electrical signal generated by motion sensor 67 is less than the threshold value, processor 60 or 80 may determine that the patient activity level associated with the seizure is relatively low and, therefore, does not conclusively indicate a convulsive motion.

In another example, processor 60 or 80 may determine whether a signal from motion sensor 67 indicates convulsive motion by correlating an amplitude waveform of the signal in the time domain or frequency domain to a template signal, determining a change in the amplitude or frequency of the electrical signal over time, comparing a ratio of power in different frequency bands to a stored value, combinations thereof, and the like. For example, a slope of the amplitude of the electrical signal from motion sensor 67 over time or timing between inflection points or other critical points in the pattern of the amplitude of the electrical signal over time may be compared to trend information. Different trends may be associated with the convulsive and nonconvulsive patient motion. Processor 60 may implement an algorithm that recognizes a trend of the electrical signal from motion sensor 67 that is indicative of a convulsive motion.

If the trend of the electrical signal from motion sensor 67 matches or substantially matches the trend template indicative of convulsive motion, processor 60 or 80 may associate the detected seizure with indication of the convulsive motion. In some examples, template correlation described herein may include correlating a signal from a motion sensor to a template or correlating a mathematically transformed signal from the motion sensor to a signal template. Processor 60 or 80 may compare the motion sensor signal or a transformed signal to a template or a transformed template. The transform may include, for example, various mathematical transforms.

The template signal or the stored values may be specific to patient 12. For example, patient 12 may undergo motion having a particular pattern during a tonic-clonic seizure, and the pattern may be captured by the template signal or stored values. A clinician may determine the template signal or stored values that indicate a particular motion associated with a seizure or a particular type of seizure during a programming session in which the signal from motion sensor 67 is monitored during one or more seizures and stored as the template. Alternatively, one or more values (e.g., amplitude values) may be extracted from the motion signal monitored during the one or more seizures of patient 12. In other examples, the template signal or the stored values may be general to more than one patient 12, such as a class of patients having similar seizure disorders.

In another example, processor 60 or 80 may perform temporal correlation with one or more templates by sampling the waveform generated by the electrical signal from the motion sensor with a sliding window and comparing the waveform with stored template waveforms that are indicative of the convulsive motion or nonconvulsive motion. In one example, processor 60 or 80 may perform a correlation analysis by moving a window along a digitized plot of the amplitude waveform of the electrical signal from motion sensor 67 at regular intervals, such as between about one millisecond to about ten millisecond intervals, to define a sample of the electrical signal. The sample window may be slid along the plot until a correlation is detected between a waveform of a template stored within memory 62 (FIG. 4) of IMD 16 or memory 82 (FIG. 5) of programmer 14 and the waveform of the sample of the electrical signal from motion sensor 67 defined by the window.

By moving the window at regular time intervals, multiple sample periods are defined. The correlation may be detected by, for example, matching multiple points between a template waveform and the waveform of the plot of the electrical signal from the motion sensor, or by applying any suitable mathematical correlation algorithm between the sample in the sampling window and a corresponding set of samples stored in the template waveform.

A sudden change in patient posture that indicates that patient 12 fell may be determined using similar techniques for detecting convulsive motion. For example, processor 60 or 80 may correlate an amplitude waveform of the signal output by motion sensor 67 in the time domain or frequency domain to a template signal that is associated with a sudden change in patient posture or a sudden movement. A correlation between the signal from motion sensor 67 and the template signal may indicate a patient fall. As another example, processor 60 or 80 may determine a change in the amplitude or frequency of the electrical signal over time and compare the change over time to a threshold value. A relatively large change in the amplitude of the electrical signal from motion sensor 61 over time may indicate a relatively sudden change in patient posture or a sudden movement, which may indicate the detected seizure is related to a fall by patient 12. Memory 62 of IMD 16 or memory 82 of programmer 14 may store the threshold value that indicates a minimum change in amplitude of electrical signal from motion sensor 61 that is associated with a relatively sudden change in patient posture or a sudden movement.

As previously described, patient posture may also be determined based on intracranial pressure of patient 12 sensed by sensing module 66 (FIG. 1) of IMD 16. A sudden change in posture (determined based on intracranial pressure) correlated with a detected seizure may indicate a patient fall.

Automatically detecting patient motion or patient posture associated with a seizure may provide more objective information about a patient's seizures than information provided by patient 12. For example, while patient 12 may indicate that patient 12 fell during a seizure, patient 12 may not be able to provide an indication of the extent of the fall. In contrast, motion sensor 67 may help identify sudden changes in patient posture that indicate a forceful fall. As another example, patient 12 may not recall undergoing involuntary movements or falling during a seizure. Thus, automatically detecting patient motion or patient posture associated with a seizure may provide a better picture of the patient's seizure than patient 12 may recollect.

FIG. 13 is a flow diagram of an example technique processor 60 may implement in order to determine a seizure metric based on patient motion associated with a detected seizure, which may include patient motion during the seizure. In the example shown in FIG. 13, the seizure metric is a seizure type, whereby a first seizure type is associated with convulsive patient motion (e.g., a clonic seizure or a tonic-clonic seizure) and a second seizure type is not associated with convulsive patient motion (e.g., an absence seizure, atonic seizure).

Processor 60 monitors patient motion (142), e.g., based on a signal generated by motion sensor 67 of IMD 16 or another motion sensor that generates a signal indicative of patient movement. Processor 60 also detects a seizure (110), e.g., using techniques described above with respect to FIG. 8. In some examples, processor 60 begins to monitor patient motion substantially continuously after detecting the seizure or at least at a higher frequency compared to the time period prior to detecting the seizure. This may help processor 60 discern relatively small changes in the patient motion during the seizure.

After detecting the seizure (110), processor 60 determines whether the patient activity level exceeds a threshold value based on the signal from motion sensor 67 (150). The threshold value may be, for example, an amplitude value that indicates an increased level of activity compared to a relatively static patient activity level. A clinician may determine the threshold value or processor 60 may automatically determine the threshold value, e.g., based on the activity of patient prior to detection of the seizure. For example, the threshold value may be an average amplitude of the signal from motion sensor 67 prior to detection of the seizure.

If the patient activity level, as indicated by a characteristic (e.g., an amplitude or change over time) of the signal from motion sensor 67, exceeds the threshold value (150), processor 60 determines that the seizure was associated with a relatively high level of activity, which may suggest the detected seizure was a convulsive seizure or a motor seizure. Thus, processor 60 categorizes the seizure as a first type (152) of seizure if the patient activity level exceeds the first threshold value. On the other hand, if the patient activity level is not greater than or equal to the threshold value, processor 60 determines that the seizure was associated with a relatively normal level of activity, which may suggest the detected seizure was not a convulsive seizure and was, for example, a sensory seizure. Thus, processor 60 categorizes the seizure as a second type (154) of seizure the patient activity level is not greater than or equal to the threshold value. The seizure types may be stored along with a seizure indication in memory 62 of IMD 16 or memory 82 of programmer.

In some examples, a clinician may wish to review information relating to seizures in which patient 12 convulsed, which may be determined based on the seizure metric indicating the seizure type. For example, the clinician may determine that the number or frequency of the seizures in which patient 12 convulsed may be useful for detecting changes in the patient condition, e.g., a progression of the patient's seizure disorder. In some examples, processor 60 of IMD 16 or processor 80 of programmer 14 may automatically generate a list, e.g., under the direction of the clinician, of the seizures that are associated with the first seizure type.

Programmer 14 or another computing device may generate a display, such as display similar to the table shown in FIG. 10, that lists a plurality of detected seizures and associated seizure metrics that are based on patient motion. The seizure metrics based on patient motion may be displayed in addition to or instead of the seizure metrics that are based on intracranial pressure.

In some cases, certain patient postures may be associated with a higher incidence of SUDEP. For example, based on SUDEP statistics, it may be determined that a large percentage of SUDEP cases occur while the patient is in a prone position (e.g., when the patient is sleeping). Accordingly, it may be useful to monitor both patient intracranial pressure and patient posture to detect a conjunction of a patient posture associated with a higher incidence of SUDEP and a relatively elevated intracranial pressure (e.g., greater than or equal to about 15 mmHg) or high intracranial pressure (e.g., greater than or equal to about 20 mmHg).

Figure 14:
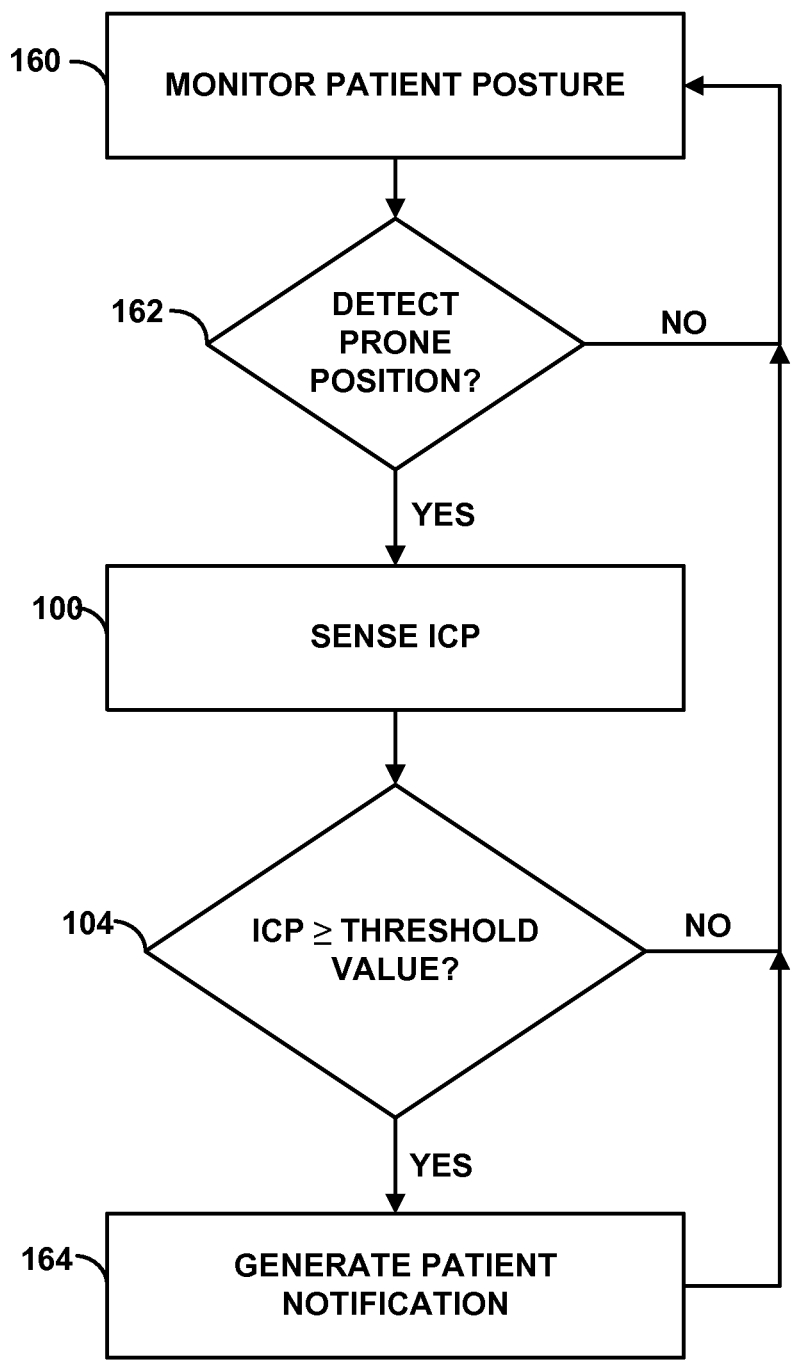
FIG. 14 is a flow diagram of an example technique for monitoring patient posture and intracranial pressure.

FIG. 14 is a flow diagram illustrating a technique for monitoring patient posture and intracranial pressure. Processor 60 of IMD 16 monitors patient posture based on electrical signals generated by motion sensor 67 (FIG. 4) (160). Based on the electrical signals, processor 60 determines whether patient 12 is in a prone position (162) or another patient posture associated with a higher incidence of SUDEP. In some examples, processor 60 determines whether patient 12 is in the prone position by comparing a characteristic of the signal generated by motion sensor 67 to a value or template stored by memory 62 (FIG. 4) of IMD 16. IMD 16 may associate the signal generated by a 3-axis accelerometer or multiple single-axis accelerometers (or a combination of a three-axis and single-axis accelerometers) with a patient posture, such as sitting, prone, recumbent, upright, and so forth.

If processor 60 determines that patient 12 is not in the prone position (162), processor 60 continues monitoring the patient posture (160). However, if processor 60 determines that patient 12 is in the prone position (162), processor 60 senses intracranial pressure (100) of patient 12. In some examples, processor 60 may begin sensing intracranial pressure of patient 12 at a higher frequency upon detecting patient 12 is in the prone position or other patient posture associated with a higher incidence of SUDEP or believed to be associated with a higher incidence of SUDEP. In other examples, processor 60 continues monitoring the intracranial pressure at substantially the same frequency.

After sensing intracranial pressure, processor 60 determines whether the intracranial pressure value is greater than or equal to a threshold value (104). The threshold value may be specific to the patient posture detected and may indicate an undesirable patient intracranial pressure when patient 12 is in the particular patient posture. As previously indicated, the intracranial pressure of patient 12 may change based on patient posture. Thus, different intracranial pressure values may be acceptable when patient 12 is in different postures. In some examples, when patient 12 is a prone position, the threshold value may be about 15 mmHg to about 20 mmHg, although other threshold values are contemplated.

If the intracranial pressure value is not greater than or equal to the threshold value (104), processor 60 continues monitoring patient posture (160) and intracranial pressure (100). On the other hand, if the intracranial pressure value greater than or equal to the threshold value (104), processor 60 generates a patient notification (164) to notify patient 12 (or a caretaker or clinician) that an undesirable intracranial pressure was detected. The notification may also indicate that patient 12 should change postures and/or seek medical attention. The patient notification may include any suitable notification, such as a somatosensory notification or auditory alert generated by IMD 16 or a visual, auditory or somatosensory alert generated by processor 14 (e.g., based on a signal received from processor 60 of IMD 16). Processor 60 may also generate and store an intracranial pressure indication, as discussed with respect to FIG. 7.

In some examples, processor 60 also generates a patient notification upon detecting the patient posture that is associated with a higher incidence of SUDEP, regardless of the intracranial pressure value sensed while patient 12 is in the patient posture. For example, patient 12 may fall asleep in one patient posture (e.g., a supine posture), but unconsciously undertake a prone position during sleep. In cases in which the prone position is associated with a higher incidence of SUDEP, IMD 16 generate a patient notification upon detecting the prone position, and transmit the notification to patient 12 via IMD 16 or via an external device, such as programmer 14 or another device near patient 12. In some examples, the patient notification may be generated immediately upon detecting the prone position or in response to detecting the prone position for a particular duration of time. The patient notification may be useful for alerting patient 12 that patient 12 is in a particular posture that is undesirable, such that patient 12 may change postures.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 60 of IMD 16 and/or processor 80 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples of the disclosure have been described. These and other examples are within the scope of the following example statements.

The invention claimed is:

1. A method comprising:
   receiving, by one or more processors and from a pressure sensor, a pressure signal indicative intracranial pressure of a patient;
   determining, with the one or more processors and based on the pressure signal, a trend in the intracranial pressure over time;
   determining, with the one or more processors, a change in a seizure disorder of the patient based on the determined trend;
   generating, with the one or more processors, an intracranial pressure indication in response to determining the change in the seizure disorder; and
   controlling, with the one or more processors, a medical device to deliver therapy to the patient based on the determined change in the seizure disorder of the patient.

2. The method of claim 1, wherein the pressure sensor is implanted within a cranium of the patient.

3. The method of claim 1, wherein the pressure signal is indicative of the intracranial pressure of the patient sensed at a frequency of at least one of once per second, once per minute, once per hour or once per day.

4. The method of claim 1, wherein the pressure signal is indicative of the intracranial pressure within a ventricle of a brain of the patient.

5. The method of claim 1, wherein determining the trend in the intracranial pressure over time comprises determining whether the intracranial pressure increases over time.

6. The method of claim 1, further comprising:
   detecting, with the one or more processors, a seizure of the patient;
   determining, with the one or more processors, a seizure metric based on the intracranial pressure indicated by the pressure signal; and
   associating, with the one or more processors, the seizure metric with the detected seizure in a memory.

7. The method of claim 6, wherein the seizure metric comprises at least one of an average intracranial pressure value sensed during the detected seizure, a median intracranial pressure value sensed during the detected seizure, or a highest intracranial pressure value sensed during the detected seizure.

8. The method of claim 6, wherein the seizure metric comprises a percent change of a value of the intracranial pressure during the detected seizure relative to a baseline value, a standard deviation of the intracranial pressure from the baseline value during the detected seizure, or a change in the intracranial pressure values over time during the detected seizure.

9. The method of claim 6, further comprising:
detecting, with the one or more processors, an intracranial pressure value that is greater than a baseline value after detecting the seizure; and
detecting, with the one or more processors, when the intracranial pressure value returns to the baseline value after detecting the seizure, wherein the seizure metric comprises a duration of time during which the intracranial pressure returned to the baseline value.

10. The method of claim 1, further comprising:
detecting, with the one or more processors, a seizure of the patient;
monitoring motion of the patient during the detected seizure; and
determining, with the one or more processors, a seizure metric based on the monitored motion.

11. The method of claim 10, further comprising determining, with the one or more processors and based on the seizure metric, that the patient experienced a change in patient posture during the seizure.

12. The method of claim 10, further comprising determining, with the one or more processors and based on the seizure metric, that the patient experienced an increase in patient motion during the seizure.

13. The method of claim 1, wherein determining the change in the seizure disorder of the patient based on the determined trend comprises determining that at least one value of the sensed intracranial pressure is greater than or equal to a threshold value.

14. The method of claim 13, wherein the threshold value is 15 millimeters of mercury (mmHg) to 20 mmHg.

15. The method of claim 13, wherein determining that the at least one value of the intracranial pressure is greater than or equal to the threshold value comprises determining that at least one of a mean intracranial pressure value or a median intracranial pressure value of a plurality of intracranial pressure values sensed over a predetermined period of time is greater than or equal to the threshold value.

16. The method of claim 13, wherein determining that the at least one value of the intracranial pressure is greater than or equal to the threshold value comprises determining that a current sensed value of the intracranial pressure is greater than or equal to the threshold value.

17. The method of claim 13, further comprising generating at least one of an audible, visible, or somatosensory notification in response to determining that the at least one value of the intracranial pressure is greater than or equal to the threshold value.

18. The method of claim 13, wherein the threshold value comprises a first threshold value, the method further comprising:
detecting, with the one or more processors, a seizure of the patient;
determining, with the one or more processors, a seizure metric based on the intracranial pressure;
after detecting the seizure, determining, with the one or more processors, whether the at least one value of the intracranial pressure is greater than or equal to a second threshold value;
generating, with the one or more processors, a first intracranial pressure category indication if the at least one value of the intracranial pressure is greater than or equal to the second threshold value;
determining, with the one or more processors, whether the value of the intracranial pressure is greater than or equal to a third threshold value if the value of the intracranial pressure is not greater than or equal to the second threshold value;
generating, with the one or more processors, a second intracranial pressure category indication if the at least one value of the intracranial pressure is greater than or equal to the third threshold value; and
generating, with the one or more processors, a third intracranial pressure category indication if the at least one value of the intracranial pressure is not greater than or equal to the third threshold value, wherein the seizure metric comprises at least one of the first, second, or third intracranial pressure category indications.

19. The method of claim 18, wherein the second threshold value is greater than the third threshold value.

20. The method of claim 1, wherein the pressure signal indicates a plurality of intracranial pressure values at a relatively high frequency, and wherein determining the trend in the sensed intracranial pressure over time comprises re-sampling the plurality of sensed intracranial pressure values post-hoc.

21. The method of claim 1, wherein the pressure signal indicates a plurality of intracranial pressure values at a relatively low frequency, and wherein determining the trend in the sensed intracranial pressure over time comprises determining the trend based on each of the plurality of sensed intracranial pressure values.

22. The method of claim 1, further comprising providing, with the one or more processors, a signal indicative of the intracranial pressure indication to an output device.

23. A system comprising:
a pressure sensor configured to sense intracranial pressure of a patient and generate a pressure signal indicative of the sensed intracranial pressure; and a processor configured to:
receive, from the pressure sensor, the pressure signal,
determine a trend in the sensed intracranial pressure over time,
determine a change in a seizure disorder of the patient based on the determined trend, and
generate an intracranial pressure indication in response to determining the change in the seizure disorder; and
a medical device configured to delivery therapy to the patient to manage the seizure disorder,
wherein the processor is further configured to control the medical device to deliver the therapy to the patient based on the determined change in the seizure disorder of the patient.

24. The system of claim 23, further comprising:
a therapy delivery element coupled to the medical device, wherein the therapy delivery element comprises the pressure sensor.

25. The system of claim 23, further comprising:
a therapy delivery element coupled to the medical device, wherein the pressure sensor is physically separate from the therapy delivery element.

26. The system of claim 23, wherein the processor is configured to determine the trend in the sensed intracranial pressure over time by at least determining whether the intracranial pressure increases over time.

27. The system of claim 23, further comprising a memory, wherein the processor is configured to detect a seizure of the patient, determine a seizure metric based on the intracranial pressure indicated by the pressure signal, and associate the seizure metric with the detected seizure in the memory.

28. The system of claim 27, further comprising a sensing module configured to sense a bioelectrical brain signal of the patient via two or more electrodes, wherein the processor is configured to detect the seizure based on the sensed bioelectrical brain signal.

29. The system of claim 27, wherein the seizure metric comprises at least one of an average intracranial pressure value sensed during the detected seizure, a median intracranial pressure value sensed during the detected seizure, or a highest intracranial pressure value sensed during the detected seizure.

30. The system of claim 27, wherein the seizure metric comprises a percent change of a value of the intracranial pressure during the detected seizure relative to a baseline value, a standard deviation of the intracranial pressure from the baseline value during the detected seizure, or a change in the intracranial pressure values over time during the detected seizure.

31. The system of claim 27, wherein the processor is configured to:
  detect an intracranial pressure value that is greater than a baseline value after detecting the seizure, and
  detect when the intracranial pressure value returns to the baseline value after detecting the seizure, wherein the seizure metric comprises a duration of time during which the intracranial pressure returned to the baseline value.

32. The system of claim 23, further comprising a motion sensor configured to generate a signal indicative of motion or posture of the patient, wherein the processor is configured to detect a seizure of the patient, monitor the signal indicative of motion or posture of the patient during the detected seizure, and determine a seizure metric based on the monitored signal indicative of motion or posture of the patient.

33. The system of claim 32, wherein the processor is configured to determine, based on the seizure metric, that the patient experienced a change in patient posture during the seizure.

34. The system of claim 32, wherein the processor is configured to determine, based on the seizure metric, that the patient experienced an increase in patient motion during the seizure.

35. The system of claim 23, wherein the processor is configured to determine the change in the seizure disorder of the patient based on the determined trend by at least determining that at least one value of the sensed intracranial pressure is greater than or equal to a threshold value.

36. The system of claim 35, wherein the threshold value is 15 millimeters of mercury (mmHg) to 20 mmHg.

37. The system of claim 35, wherein the processor is configured to determine that the at least one value of the intracranial pressure is greater than or equal to the threshold value by at least determining that at least one of a mean intracranial pressure value or median intracranial pressure value of a plurality of intracranial pressure values sensed over a predetermined period of time is greater than or equal to the threshold value.

38. The system of claim 35, wherein the processor is configured to generate a user notification if the value of the sensed intracranial pressure is greater than or equal to the threshold value.

39. The system of claim 38, further comprising a user interface configured to transmit the user notification to a user, wherein the user notification comprises at least one of a visual, auditory or somatosensory alert.

40. The system of claim 38, wherein the processor is configured to generate the user notification by at least causing the medical device to vibrate or generate an audible sound.

41. The system of claim 35, wherein the threshold value comprises a first threshold value, the processor further configured to detect a seizure of the patient, determine a seizure metric based on the sensed intracranial pressure, determine whether the at least one value of the intracranial pressure is greater than or equal to a second threshold value after detecting the seizure, generate a first intracranial pressure category indication if the at least one value of the intracranial pressure is greater than or equal to the second threshold value, determine whether the at least one value of the intracranial pressure is greater than or equal to a third threshold value if the at least one value of the intracranial pressure is not greater than or equal to the second threshold value, generate a second intracranial pressure category indication if the at least one value of the intracranial pressure is greater than or equal to the third threshold value, and generate a third intracranial pressure category indication if the at least one value of the intracranial pressure is not greater than or equal to the third threshold value, wherein the seizure metric comprises at least one of the first, second, or third intracranial pressure category indications.

42. The system of claim 23, wherein the pressure sensor is configured to sense intracranial pressure of the patient by at least sensing a plurality of intracranial pressure values at a relatively high frequency, and wherein the processor is configured to determine the trend in the sensed intracranial pressure over time by at least re-sampling the plurality of sensed intracranial pressure values post-hoc.

43. The system of claim 23, wherein the pressure sensor is configured to sense intracranial pressure of the patient by at least sensing a plurality of intracranial pressure values at a relatively low frequency, and wherein the processor is configured to determine the trend in the sensed intracranial pressure over time by at least determining the trend based on each of the plurality of sensed intracranial pressure values.

44. The system of claim 23, wherein the processor is further configured to adjust the delivery of the therapy by the medical device to the patient based on the determined change in the seizure disorder of the patient.

45. The system of claim 23, wherein the processor is further configured to provide a signal indicative of the intracranial pressure indication to an output device.

46. A system comprising:
  means for sensing intracranial pressure of a patient;
  means for determining a trend in the sensed intracranial pressure over time;
  means for determining a change in a seizure disorder of the patient based on the determined trend;
  means for generating an intracranial pressure indication in response to the determination of the change in the seizure disorder;
  means for delivering therapy to the patient to manage the seizure disorder; and
  means for controlling the means for delivering therapy to deliver therapy to the patient based on the determined change in the seizure disorder of the patient.

47. The system of claim 46, further comprising:
  means for detecting a seizure of the patient;
  means for determining a seizure metric based on the sensed intracranial pressure; and
  means for associating the seizure metric with the detected seizure in a memory.

48. The system of claim 46, further comprising:
means for monitoring motion of the patient; and
means for determining a seizure metric based on the monitored motion of the patient.

49. The system of claim 46, wherein the means for determining the change in the seizure disorder of the patient based on the determined trend comprises means for determining that a value of the sensed intracranial pressure is greater than or equal to a threshold value.

50. The system of claim 46, further comprising means for providing a signal indicative of the intracranial pressure indication to an output device.

* * * * *

UNITED STATES PATENT AND TRADEMARK OFFICE
CERTIFICATE OF CORRECTION

PATENT NO. : 10,369,353 B2
APPLICATION NO. : 12/359037
DATED : August 6, 2019
INVENTOR(S) : Giftakis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2931 days.

Signed and Sealed this
Sixteenth Day of June, 2020

Andrei Iancu
*Director of the United States Patent and Trademark Office*